United States Patent [19]

Pittet et al.

[11] Patent Number: 4,590,082

[45] Date of Patent: May 20, 1986

[54] FLAVORING WITH CYCLOALKYL ESTERS OF MERCAPTOALKANOIC ACIDS

[75] Inventors: Alan O. Pittet, Atlantic Highlands; Ranya Muralidhara, Fair Haven; Manfred H. Vock, Locust; Kevin P. Miller, Middletown; Domenick Luccarelli, Jr., Neptune; Charles Wiener, Middletown, all of N.J.

[73] Assignee: International Flavors & Fragrances Inc., New York, N.Y.

[21] Appl. No.: 768,706

[22] Filed: Aug. 23, 1985

[51] Int. Cl.$^4$ .................. A23L 1/226; A23L 1/231; A23L 1/235

[52] U.S. Cl. ........................ 426/535; 560/152

[58] Field of Search ................ 426/535; 560/152

[56] References Cited

U.S. PATENT DOCUMENTS

| | | | |
|---|---|---|---|
| 3,870,800 | 3/1975 | Pittet et al. | 426/535 |
| 3,879,562 | 4/1975 | Pittet et al. | 426/535 |
| 3,904,556 | 9/1975 | Pittet et al. | 560/152 X |
| 4,096,284 | 6/1978 | Greenberg | 426/535 |
| 4,162,335 | 7/1979 | Wilson et al. | 426/535 |
| 4,426,403 | 1/1984 | Cyronak et al. | 426/535 |

*Primary Examiner*—Joseph Golian
*Attorney, Agent, or Firm*—Arthur L. Liberman

[57] ABSTRACT

Described are the cycloalkyl esters of mercaptoalkanoic acids defined according to the structure:

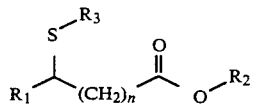

wherein $R_1$ represents hydrogen or methyl; $R_2$ represents mono $C_1$-$C_4$ alkyl substituted or unsubstituted $C_5$-$C_8$ cycloalkyl; $R_3$ represents hydrogen or methyl; and N represents 0, 1 or 2 and uses thereof in augmenting or enhancing the aroma or taste of foodstuffs.

17 Claims, 37 Drawing Figures

GLC PROFILE FOR EXAMPLE I(A).
CRUDE

FIG. 2 NMR SPECTRUM FOR EXAMPLE I(A).

FIG. 3 NMR SPECTRUM FOR EXAMPLE I(B).

GLC PROFILE FOR EXAMPLE II.
CRUDE

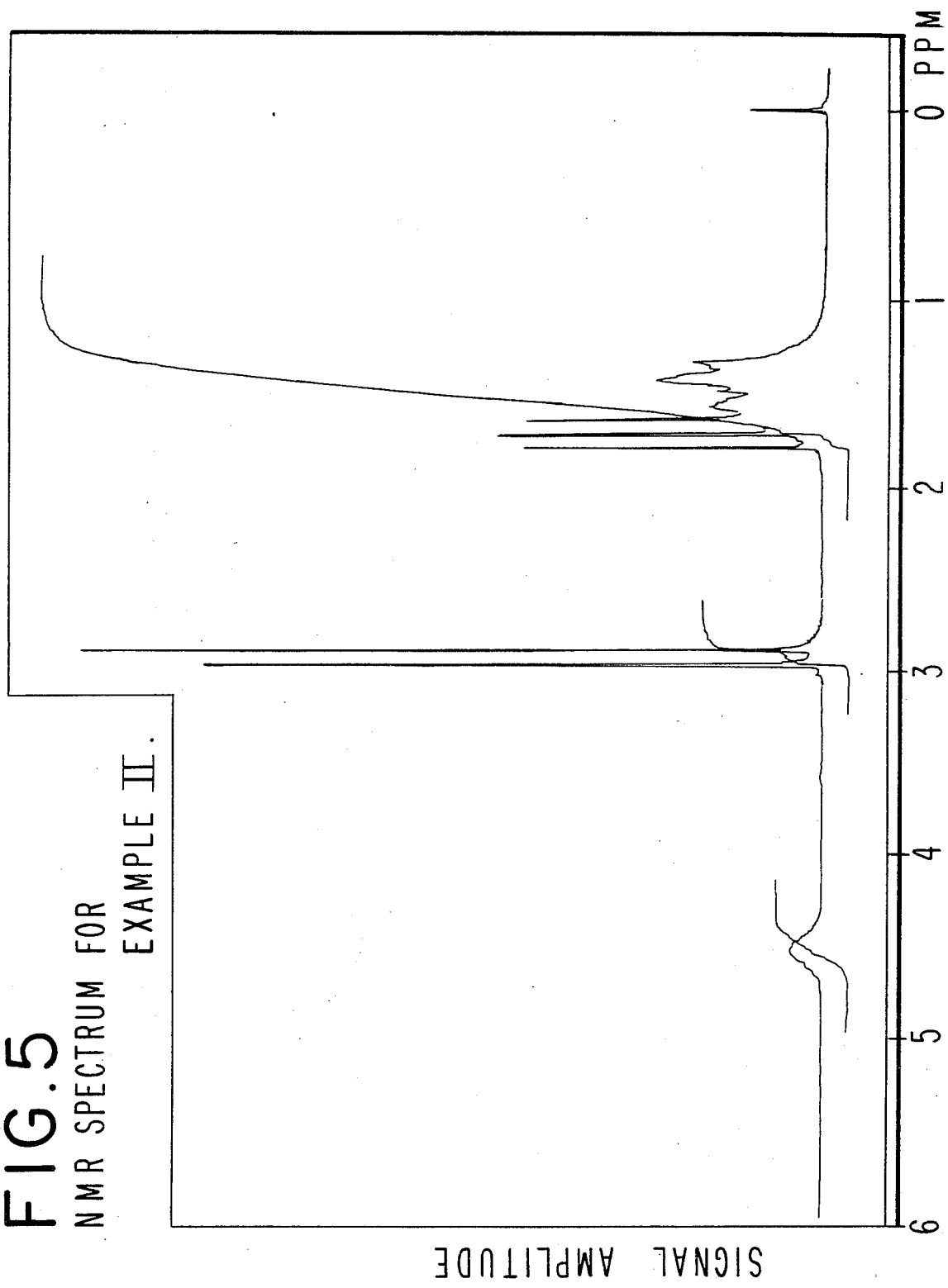

GLC PROFILE FOR FRACTION 15 OF EXAMPLE IV(B).

GLC PROFILE FOR EXAMPLE III CRUDE

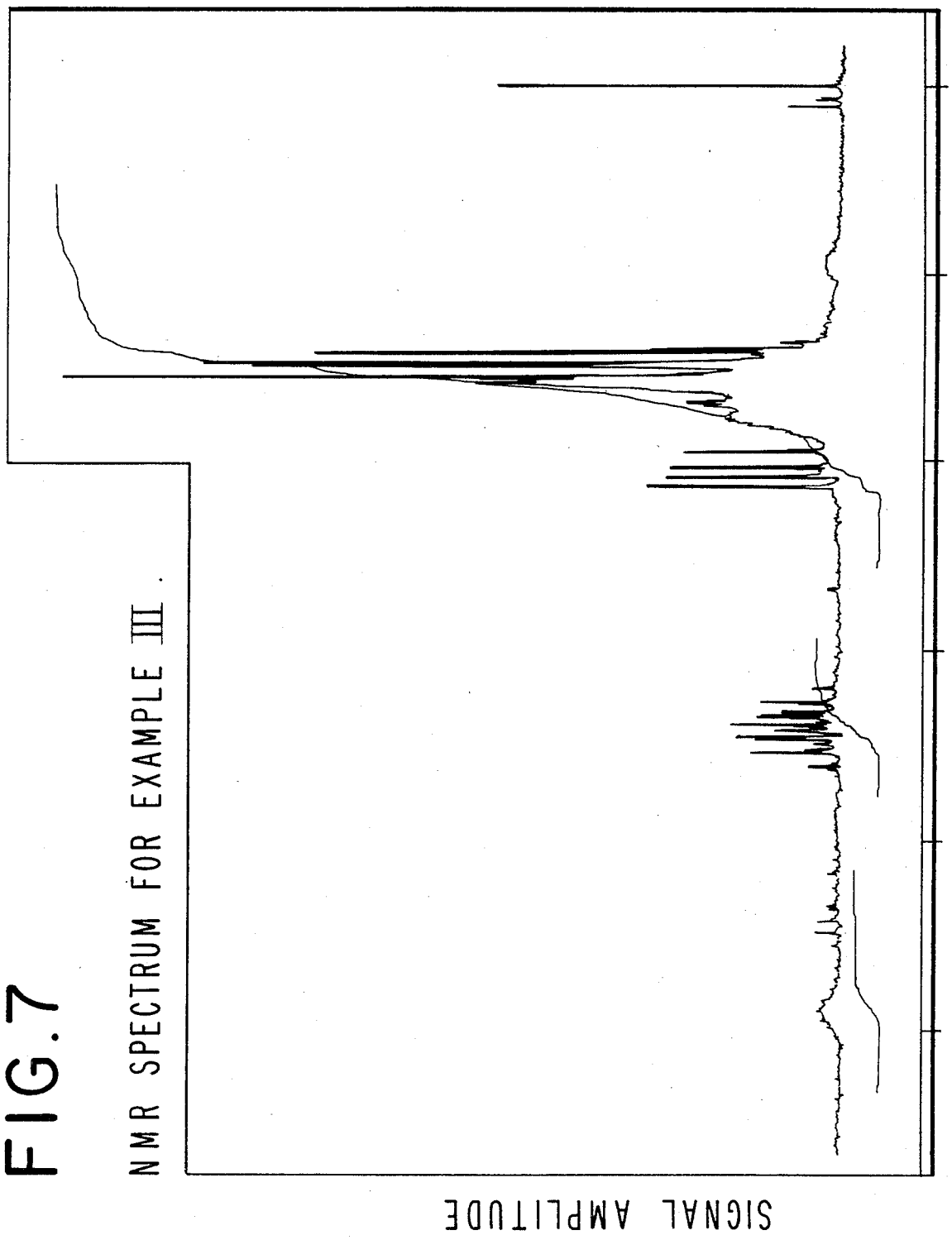
FIG. 7 NMR SPECTRUM FOR EXAMPLE III

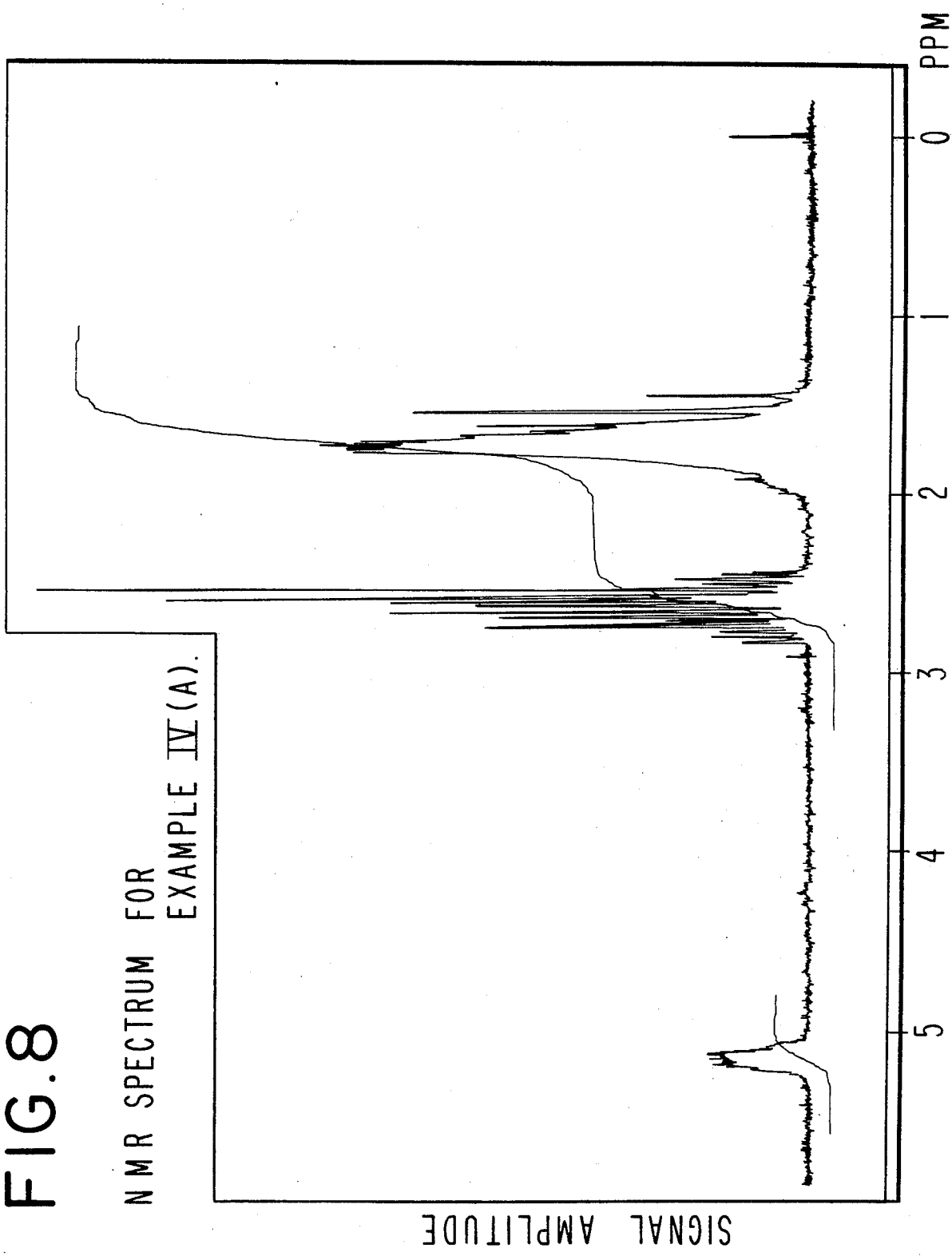
FIG. 8 NMR SPECTRUM FOR EXAMPLE IV(A).

GLC PROFILE FOR FRACTION 16 OF EXAMPLE IV(B).

GLC PROFILE FOR FRACTION 8 OF EXAMPLE IV(B).

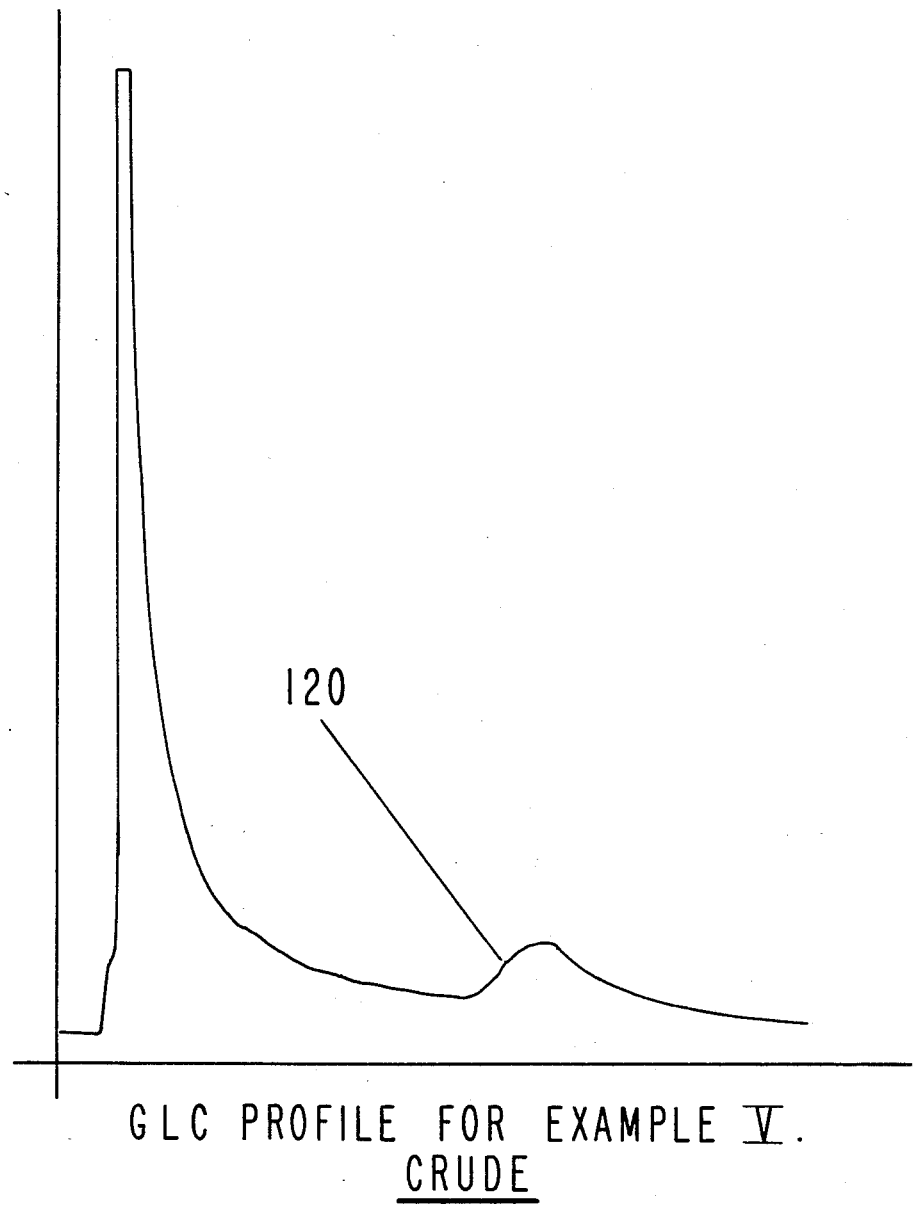

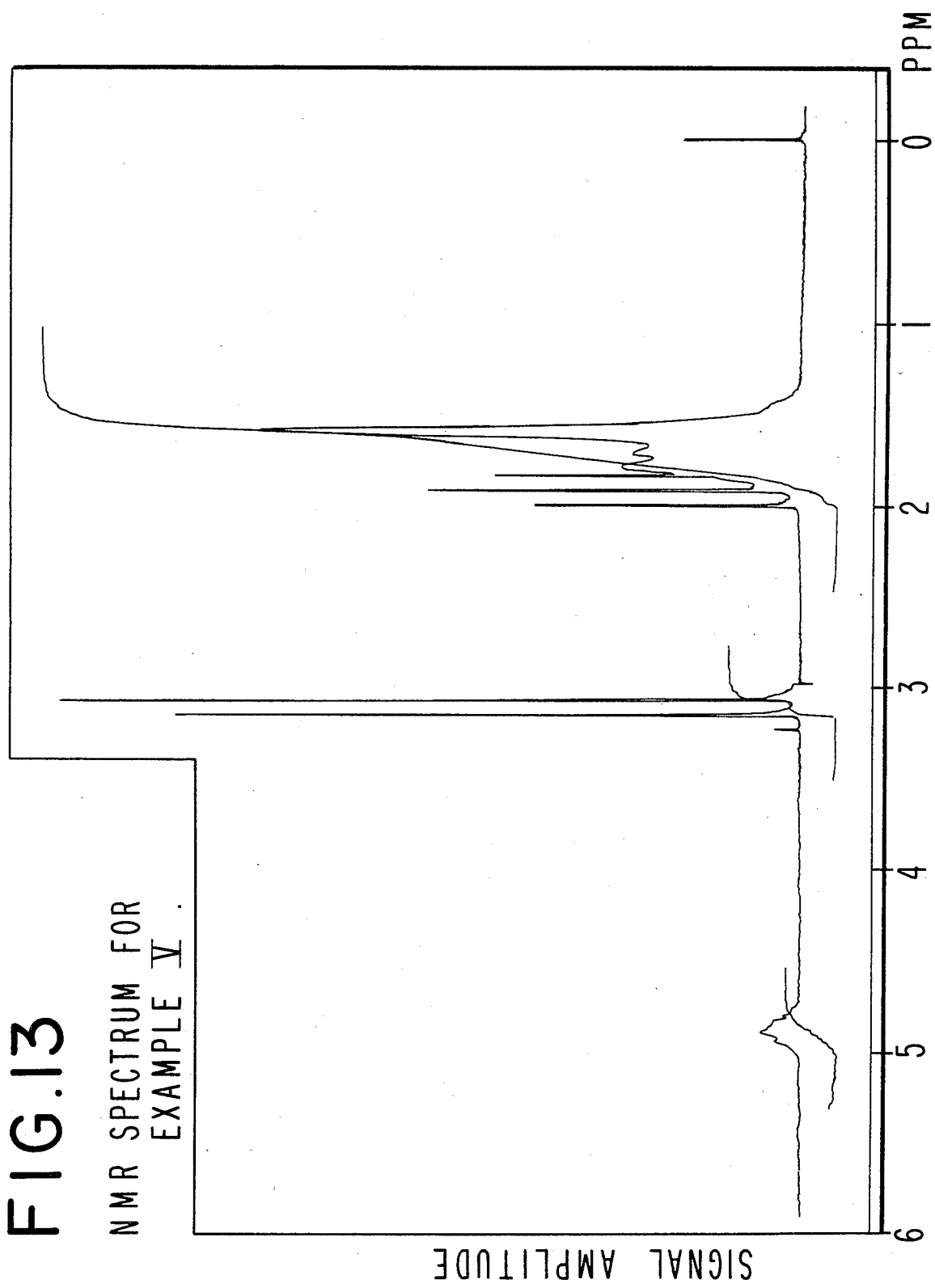
FIG.13 NMR SPECTRUM FOR EXAMPLE V.

GLC PROFILE FOR EXAMPLE VIII.
CRUDE

GLC PROFILE FOR EXAMPLE VI.
CRUDE

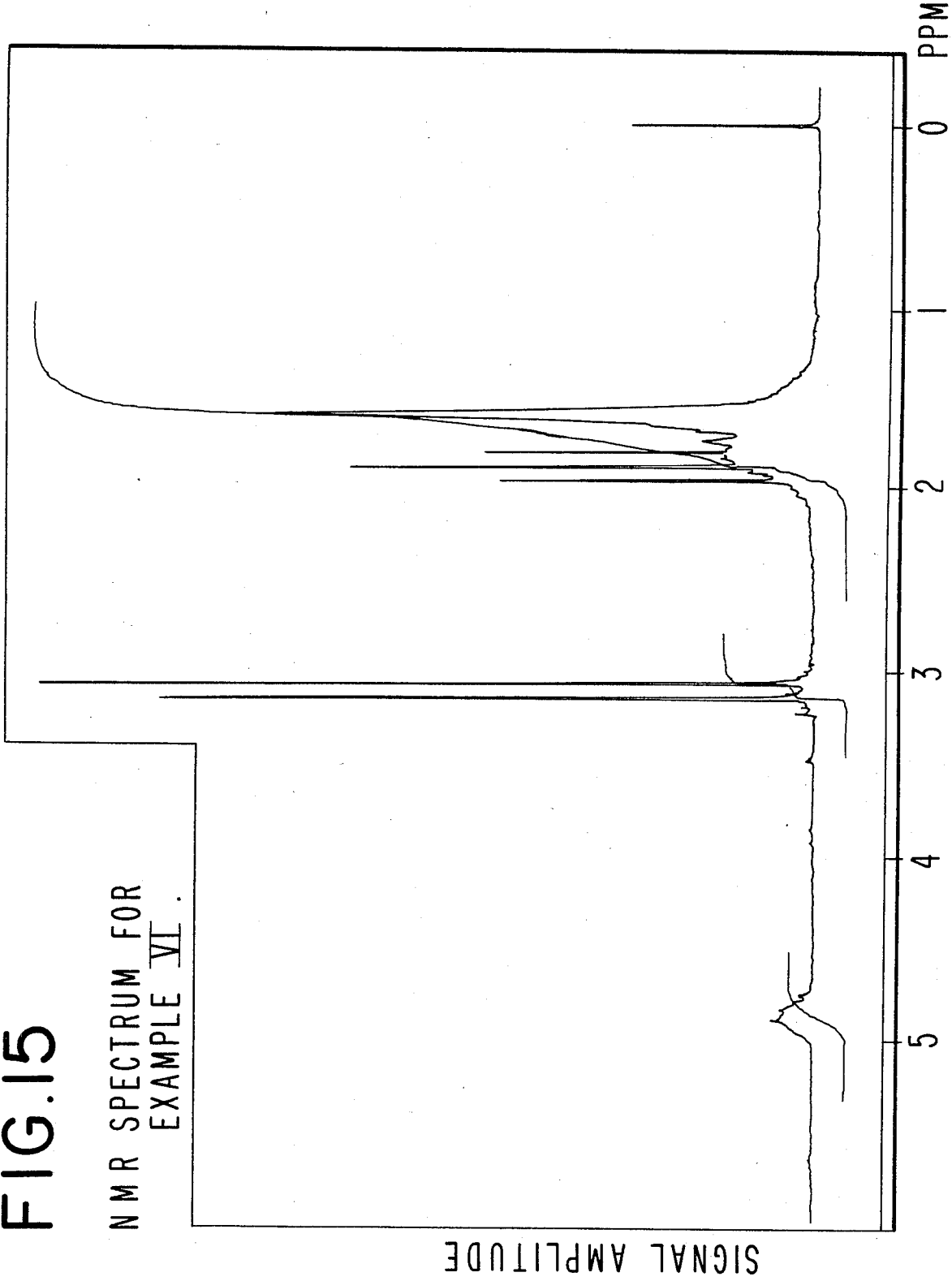
FIG.15 NMR SPECTRUM FOR EXAMPLE VI.

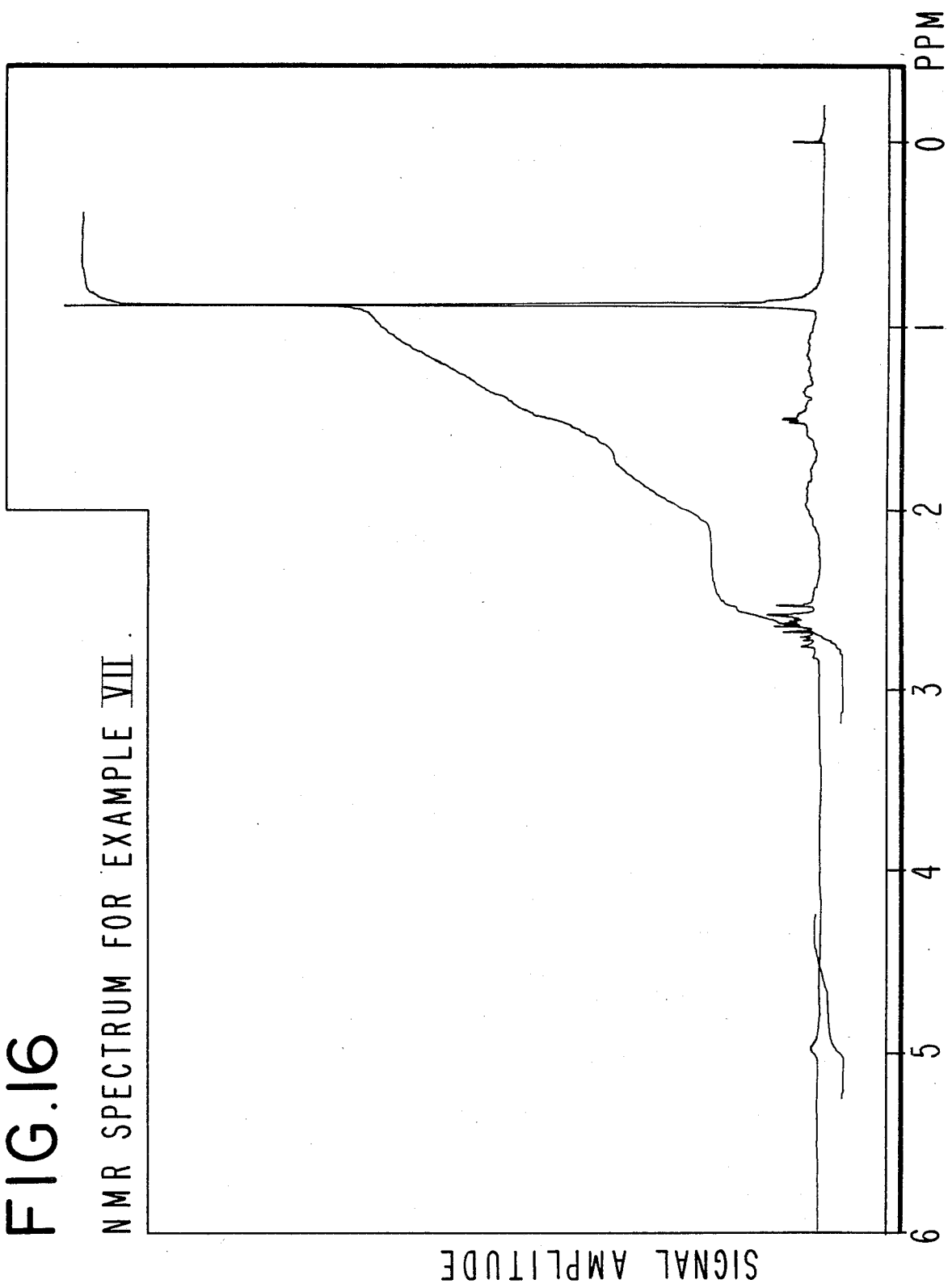
FIG.16 NMR SPECTRUM FOR EXAMPLE VII

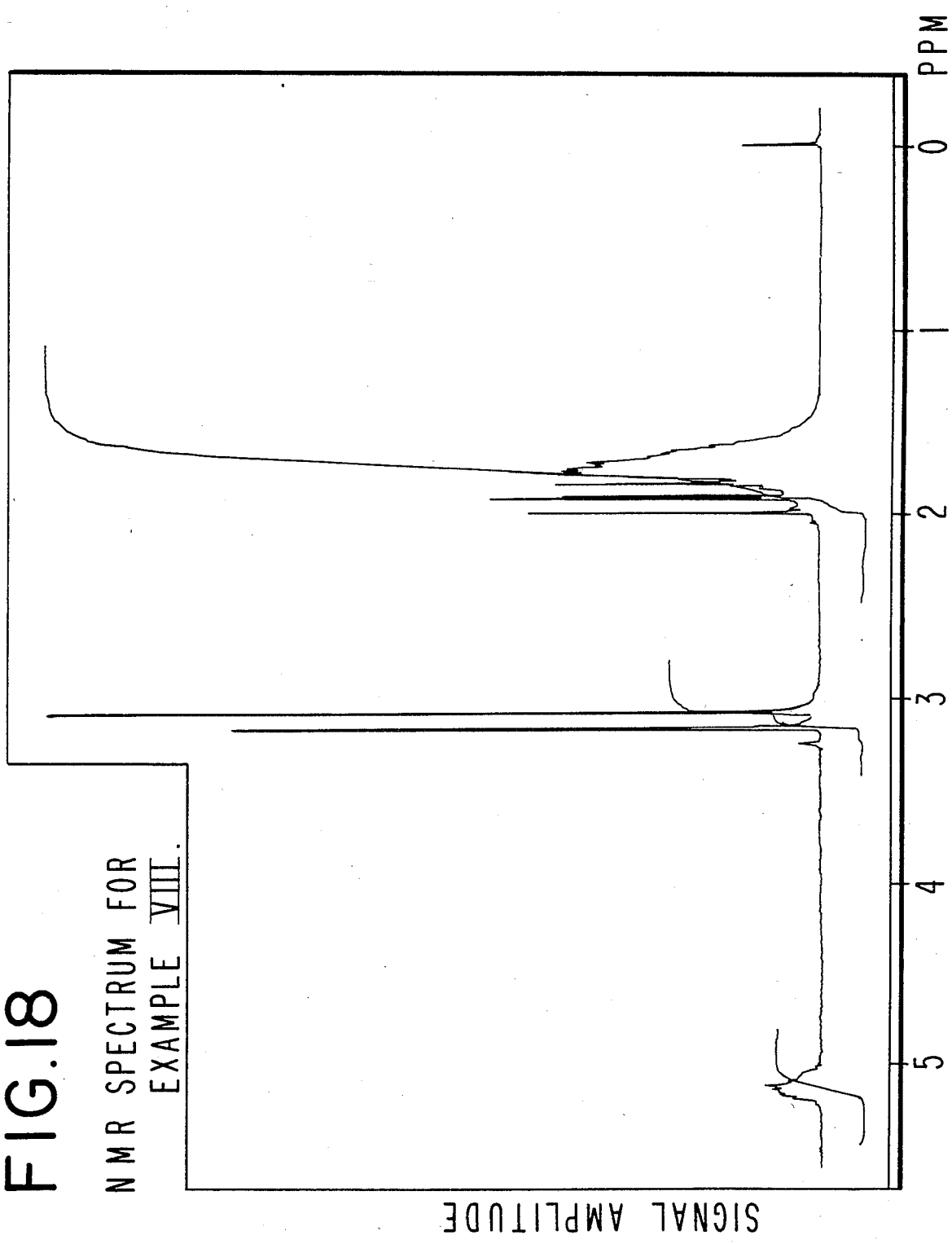
FIG. 18 NMR SPECTRUM FOR EXAMPLE VIII.

GLC PROFILE FOR EXAMPLE XI. CRUDE

GLC PROFILE FOR EXAMPLE IX. CRUDE

FIG. 20 NMR SPECTRUM FOR EXAMPLE IX

NMR SPECTRUM FOR EXAMPLE X.

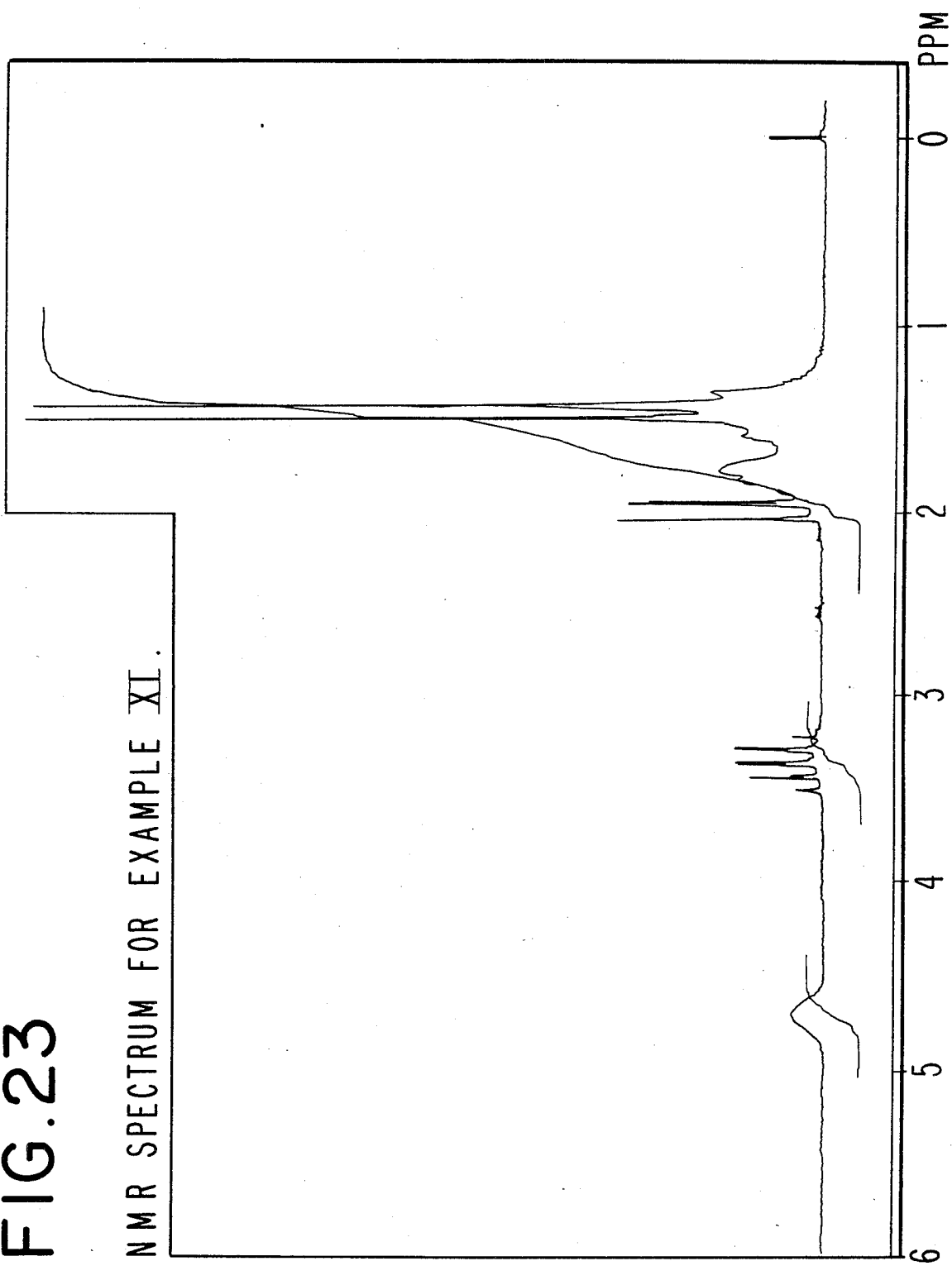
FIG. 23 NMR SPECTRUM FOR EXAMPLE XI.

GLC PROFILE FOR FRACTION 4 OF EXAMPLE XIV.

GLC PROFILE FOR EXAMPLE XII. CRUDE

FIG. 25 NMR SPECTRUM FOR EXAMPLE XII.

NMR SPECTRUM FOR EXAMPLE XIII.

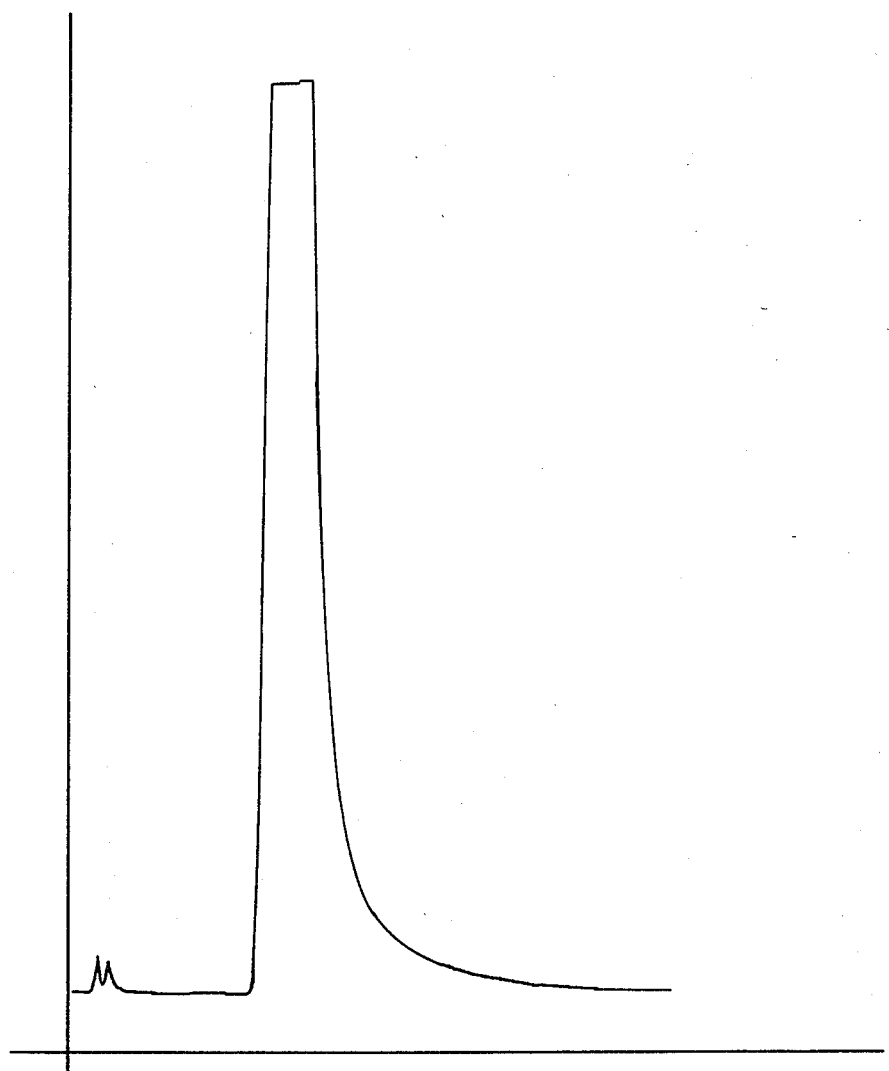

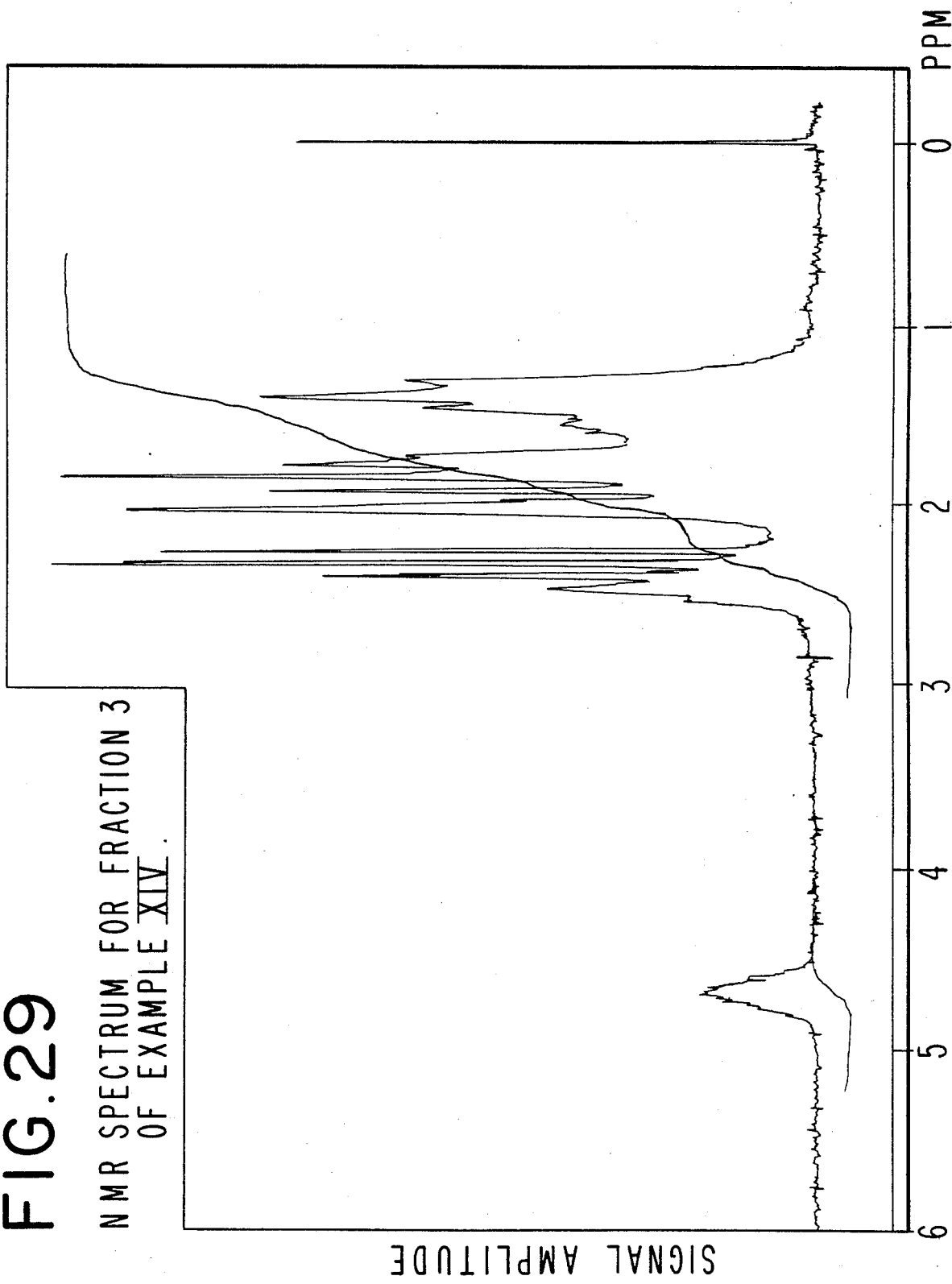
FIG. 29 NMR SPECTRUM FOR FRACTION 3 OF EXAMPLE XIV.

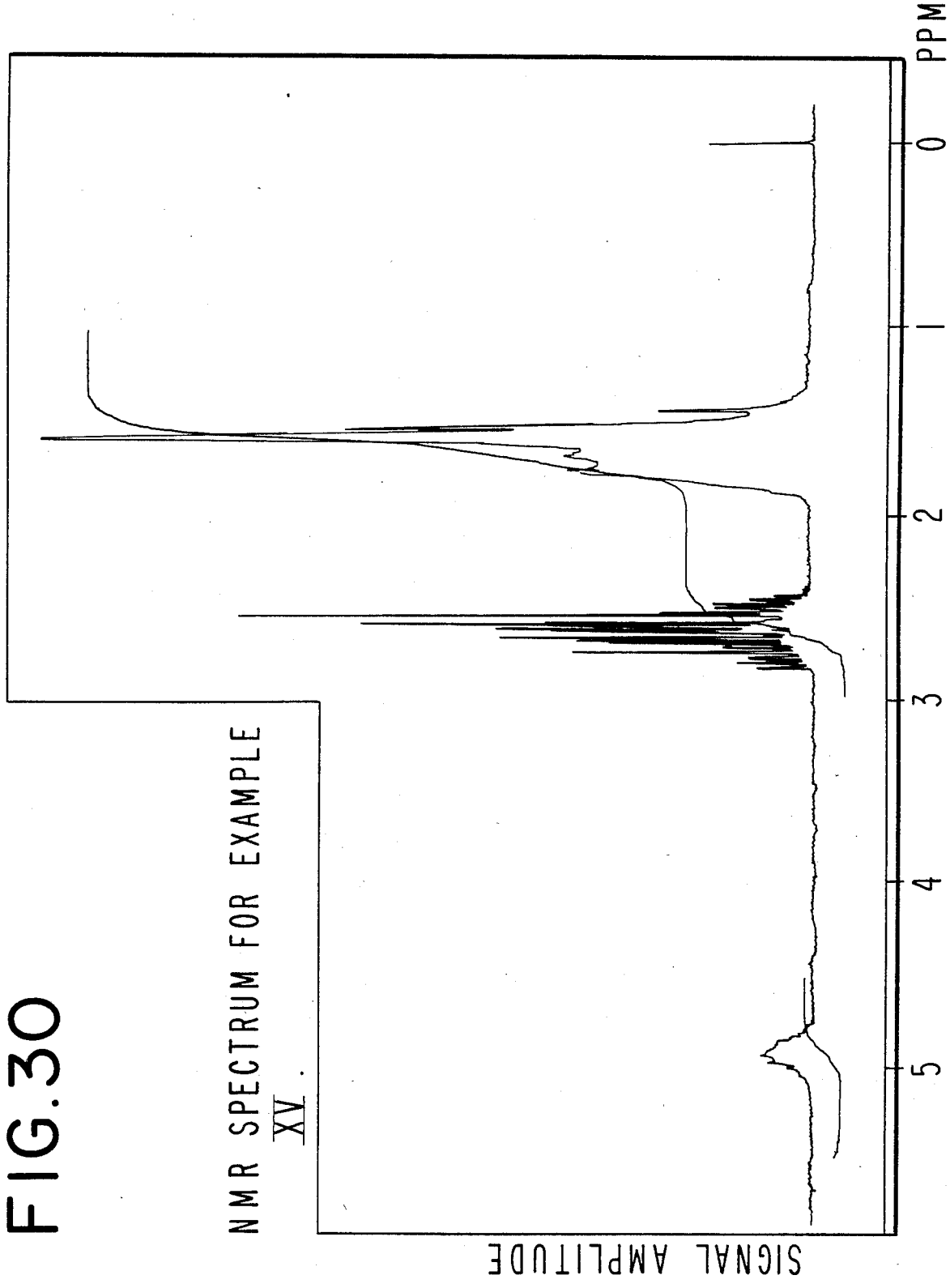
FIG. 30 NMR SPECTRUM FOR EXAMPLE XV

GLC PROFILE FOR FRACTION 3 OF EXAMPLE XXII

GLC PROFILE FOR EXAMPLE XXII CRUDE

GLC PROFILE FOR FRACTION 5 OF EXAMPLE XXII.

GLC PROFILE FOR FRACTION 4 OF EXAMPLE XXII

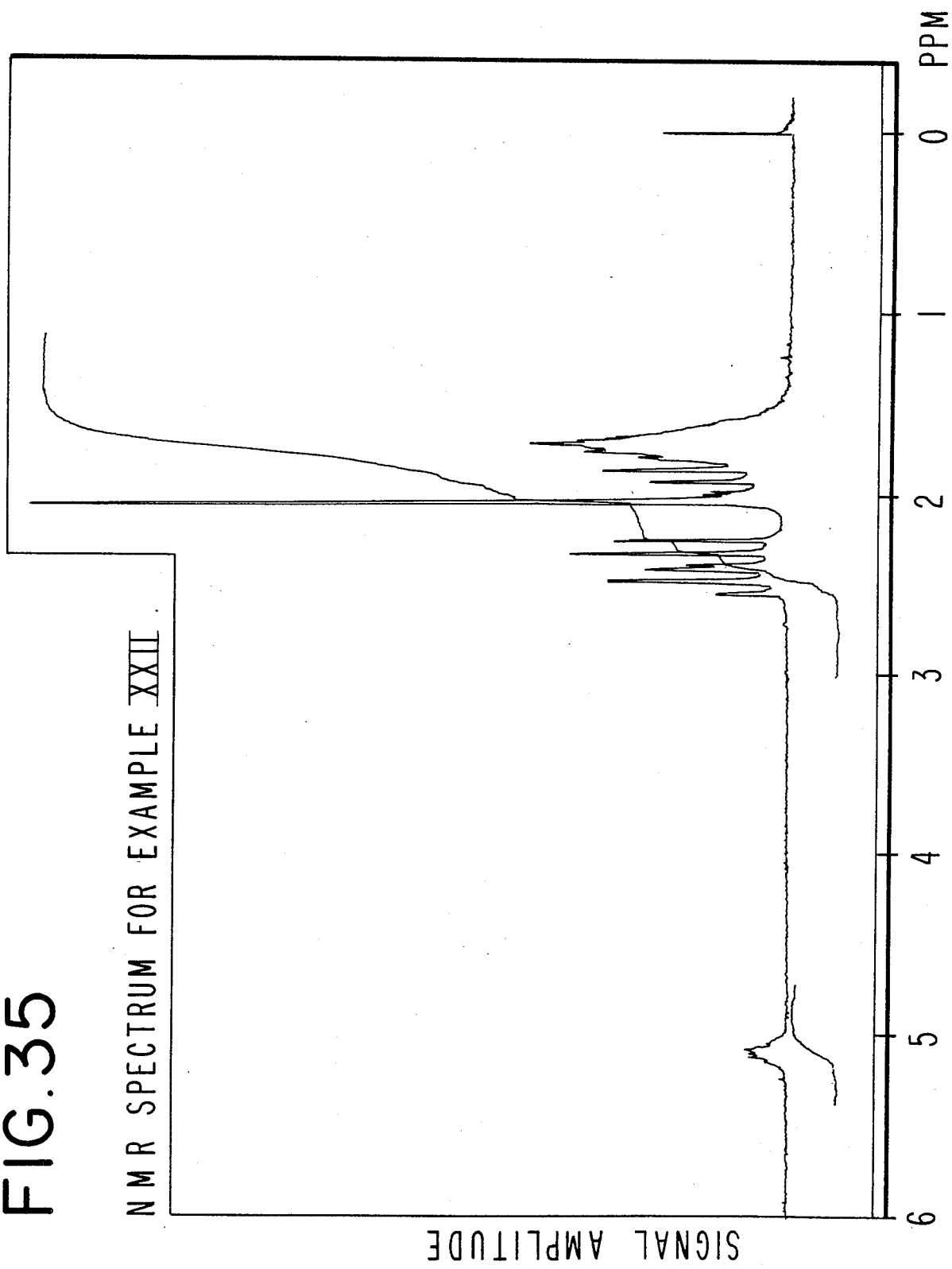
FIG. 35 NMR SPECTRUM FOR EXAMPLE XXII

GLC PROFILE FOR FRACTION 4 OF EXAMPLE XXIII.

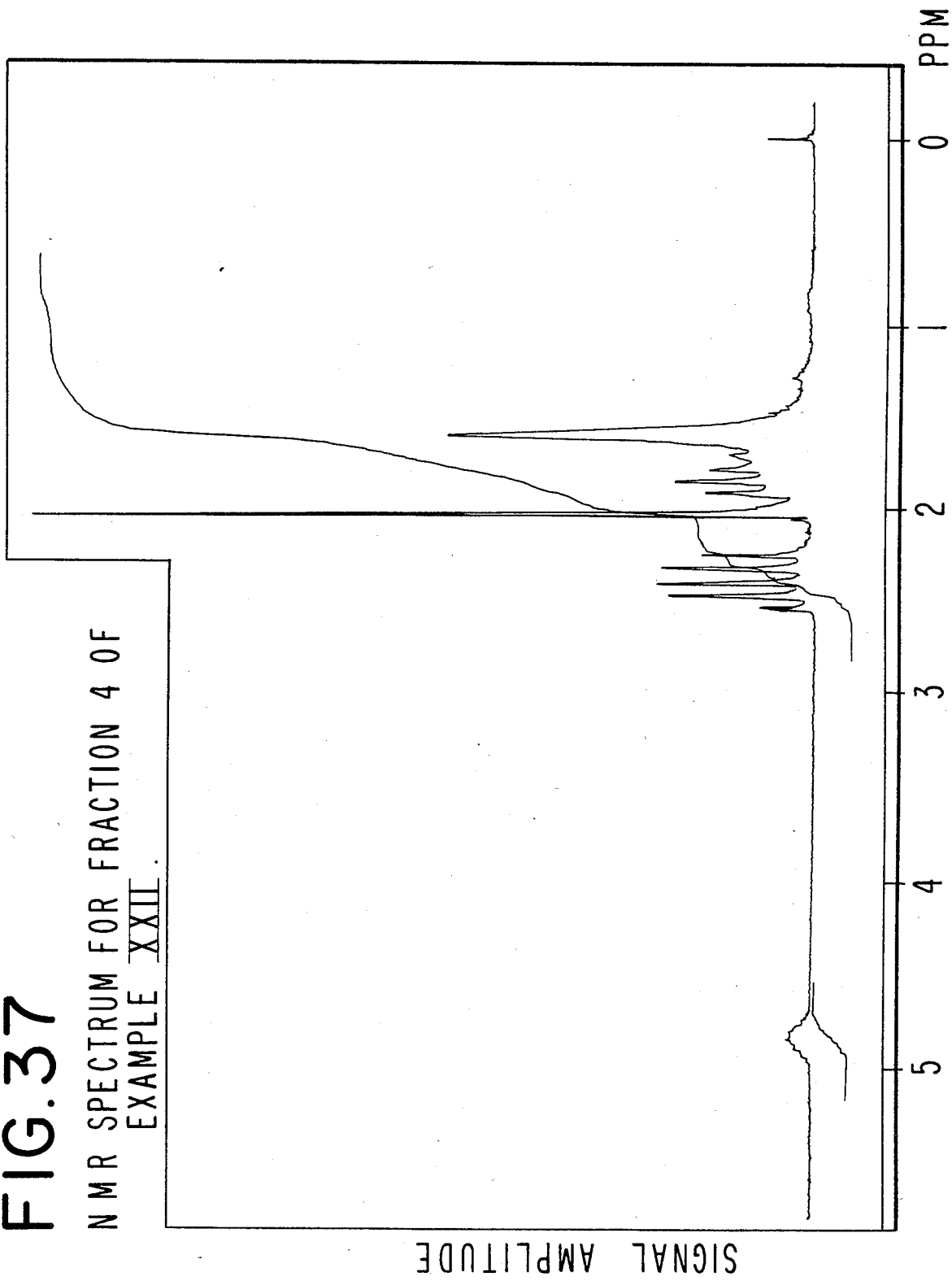
FIG. 37 NMR SPECTRUM FOR FRACTION 4 OF EXAMPLE XXII

FLAVORING WITH CYCLOALKYL ESTERS OF MERCAPTOALKANOIC ACIDS

BACKGROUND OF THE INVENTION

The present invention relates to cycloalkyl esters of mercaptoalkanoic acids defined according to the structure:

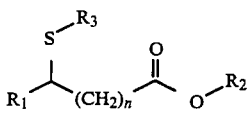

wherein $R_1$ represents hydrogen or methyl; $R_2$ represents mono $C_1$–$C_4$ alkyl substituted or unsubstituted $C_5$–$C_8$ cycloalkyl; $R_3$ represents hydrogen or methyl; and N represents 0, 1 or 2 and uses thereof in augmenting or enhancing the aroma or taste of foodstuffs.

Artificial flavoring agents for foodstuffs have received increasing attention in recent years. In many areas, such food flavoring agents are preferred over natural flavoring agents at least in part, because of the uniform flavor that may be so obtained. For example, natural food flavoring agents such as extracts, essences, concentrates and the like are often subject to wide variations due to changes in quality and type and treatment of the raw materials. Such variations can be reflected in the end product and results in unreliable flavor characteristics and uncertainty as to consumer acceptance cost. Additionally, the presence of the natural product in the ultimate food may be undesirable because of the increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having roasted, roasted sesame, roasted peanut, concord grape, burnt potato skin, cashew juice, roasted almond, roasted meat, peanut, Yeasty, cashew, fruity, kiwi-like, citrus, boiled corn, boiled green bean, cooked ham, bread crust, pineapple, roasted nut, grapefruit, meaty, sesame, oniony and roasted onion aroma and taste nuances.

Reproduction of roasted, roasted sesame, roasted peanut, sulfury, concord grape, burnt potato skin, cashew juice, roasted almond, pineapple, roasted nut, grapefruit, meaty, sesame, oniony, roasted onion, floral, roasted meat, peanut, yeasty, cashew, bread crust, fruity, green, kiwi-like, citrus, boiled corn, boiled green bean and cooked ham aroma and taste nuances has been the subject of long and continuous searches by those engaged in the production of foodstuffs. The severe shortage of food, especially protein foods, in many parts of the world has given rise to the need for utilizing non-meat sources of proteins and making such proteins as palatable as possible. Hence, materials which will closely simulate or exactly reproduce the flavor and aroma of peanut, almond, sesame, potato, concord grape, cashew juice, roasted almond, caramel, roasted meat, roasted nut, cashew, yeast, kiwi, citrus, cooked vegetables, cooked ham, pineapple, grapefruit and durian are required. Furthermore, meat flavors and vegetable flavors have been enhanced previously by the use of such materials as monosodium glutamate. In many diets, sodium is not desired. Furthermore, in many diets, the use of glutamate ion or glutamic acid is highly undesirable. Therefore a need has arisen for a monosodium glutamate replacer and an alkali metal glutamate replacer which does not have any glutamate ion or any sodium ion present.

Moreover, there are a great many meat containing or meat based foods presently distributed in a preserved form. Examples of these are condensed soups, dry soup mixes, dry meat, freeze dried or lyophilized meats, packaged gravies and the like. While these products contain meat or meat extracts, the fragrance, taste and other organoleptic factors are often impaired by the processing operation and it is desirable to supplement or enhance the flavors of these preserved foods with versatile materials which have roasted, roasted meat and roasted nut aroma and taste nuances.

Food flavors in the thioalkanoic acid ester area are known in the prior art.

Thus, U.S. Pat. No. 4,426,403 discloses the genus of compounds defined according to the structure:

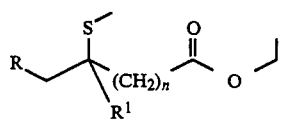

wherein R and R' represent hydrogen or $C_1$–$C_3$ alkyl as food flavorants, particularly in the fruity, vegetable or green pine needle aroma and taste area.

U.S. Pat. No. 3,870,800 relates to the processes for augmenting or enhancing the aroma or taste of foodstuffs using methylthio butanoic acid derivatives. U.S. Pat. No. 3,904,556, at Example XVII thereof states that ethyl-4-(methylthio)butyrate may be added to a cheese sauce to increase the notes usually present in the surface ripened cheese and to increase the cheese flavor intensity. In Example XX it is further stated that this compound, ethyl-4-(methylthio)butyrate is added to tobacco to enhance the pineapple character of a fruit flavor for tobacco.

U.S. Pat. No. 3,879,562 issued on Apr. 22, 1975 and the reissue patent thereof, U.S. Pat. No. Re. 30,370 issued on Aug. 12, 1980 disclose the genus of compounds having the structure:

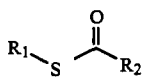

wherein $R_1$ represents alkyl, cyckloalkyl, aryl, aralkyl, alkaryl, or alkenyl and $R_2$ represents alkyl, alkyl thioalkyl, aralkyl, alkaryl or aryl in augmenting or enhancing the aroma or taste of various foodstuffs.

McFadden, et al, Analytical Chemistry 37,560, have suggested the presence of methyl thiohexanoate and thioheptanoate in oil derived from hops, and Buttery, et al, have reported similar work in J. Chromatography 18,399. Schultz, Day and Libbey, "The Chemistry and Physiology of Flavors", Westport, Conn.:Avi. Publishing Company, 1967, at page 412 disclose thioesters useful in flavoring.

Nevertheless, nothing in the prior art discloses the cycloalkyl esters of mercaptoalkanoic acids of our invention or their unexpected, unobvious and advantageous uses in augmenting or enhancing the aroma or taste of foodstuffs.

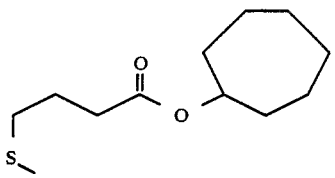

(Conditions: 8'×0.125" SE-30 column programmed at 220° C. isothermal).

Figure 2:
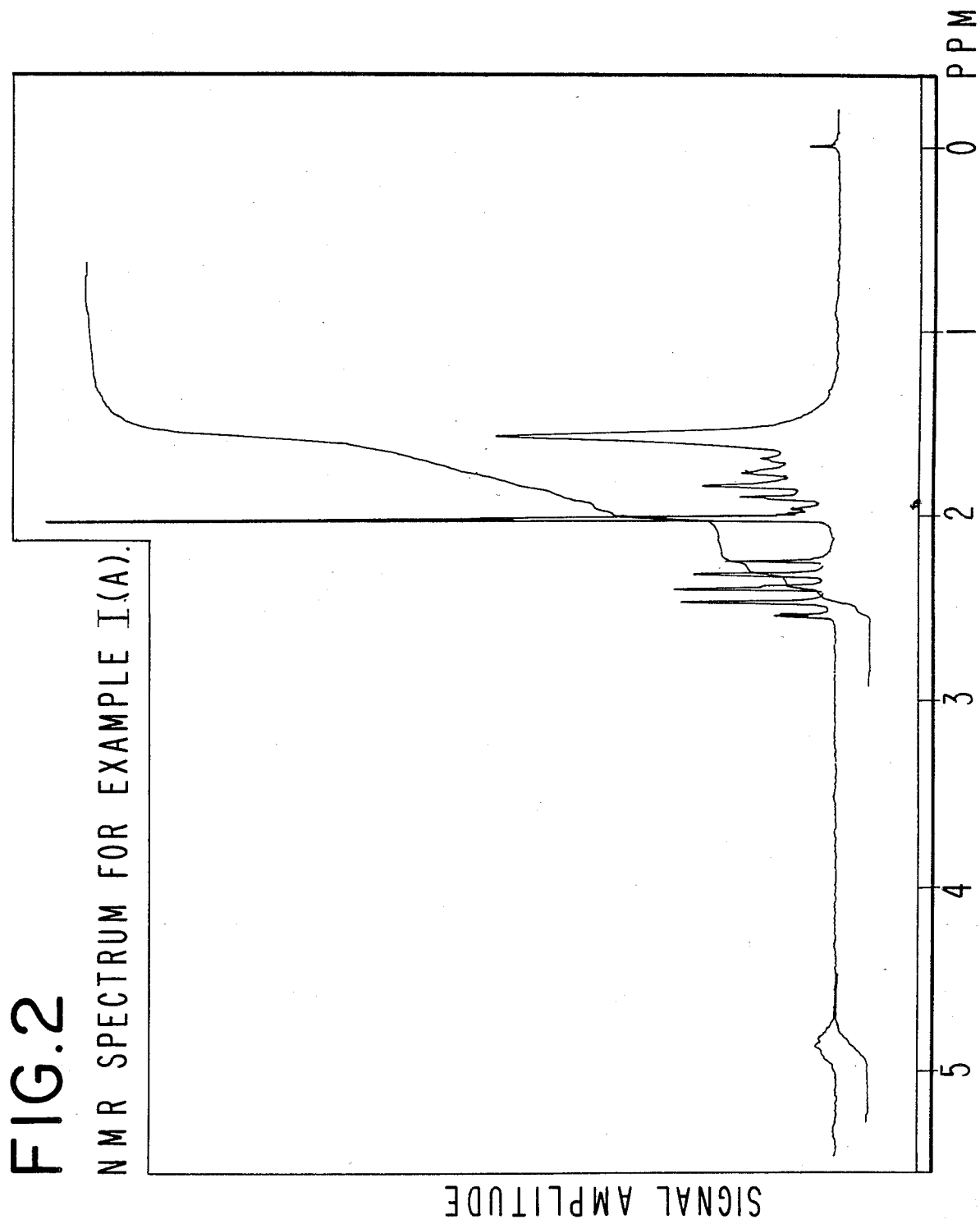

FIG. 2 is the NMR spectrum for the compound having the structure:

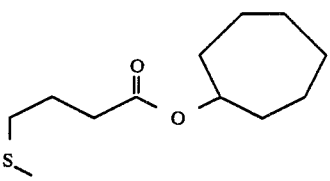

produced according to Example I(A)(Conditions: Field strength: 100 MHz; Solvent: CFCl₃).

Figure 3:
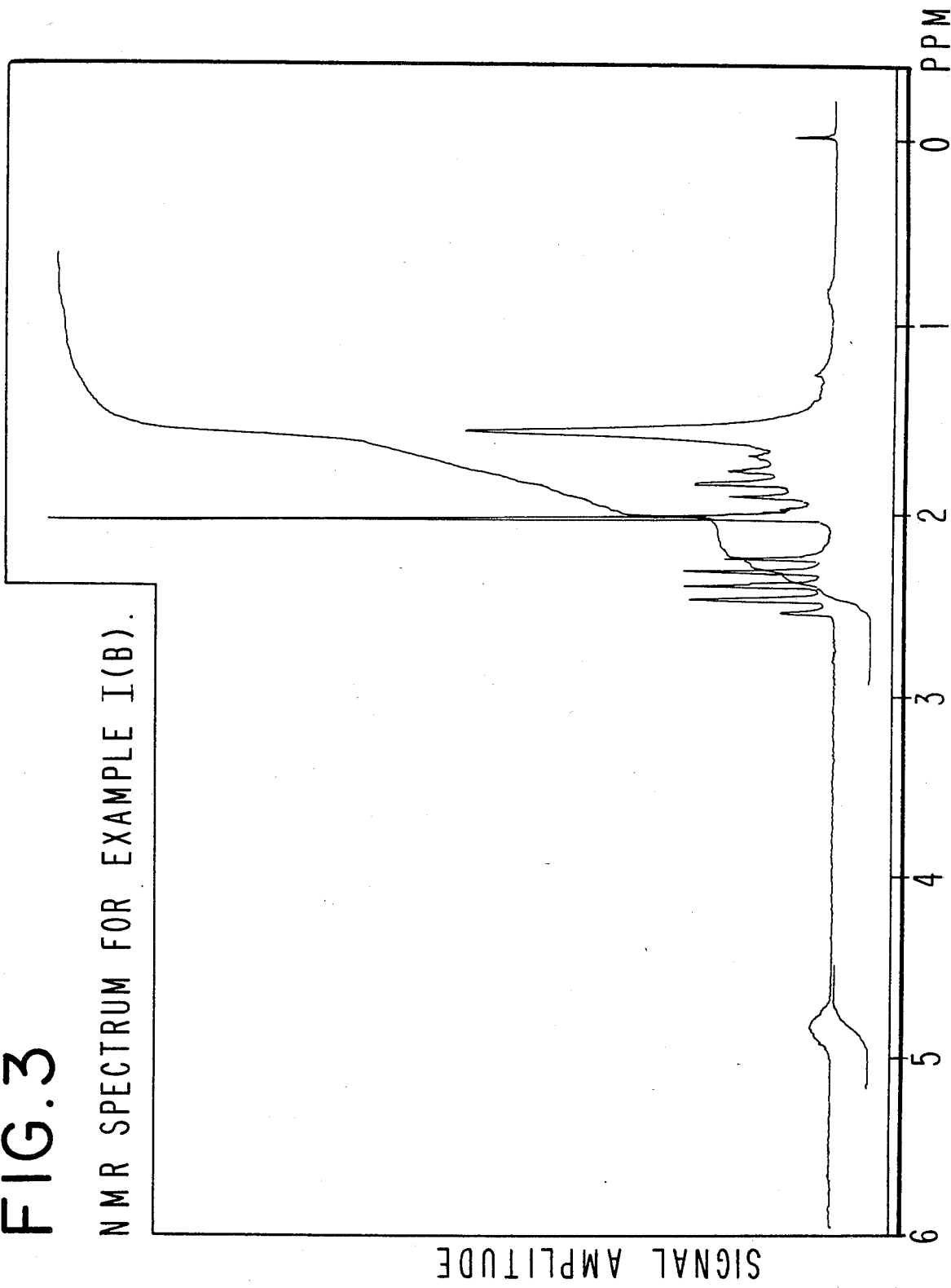

FIG. 3 is the NMR spectrum for the compound having the structure:

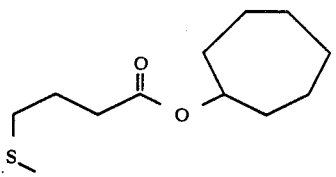

prepared according to Example I(B)(Conditions: Field strength: 100 MHz; Solvent: CFCl₃).

Figure 4:
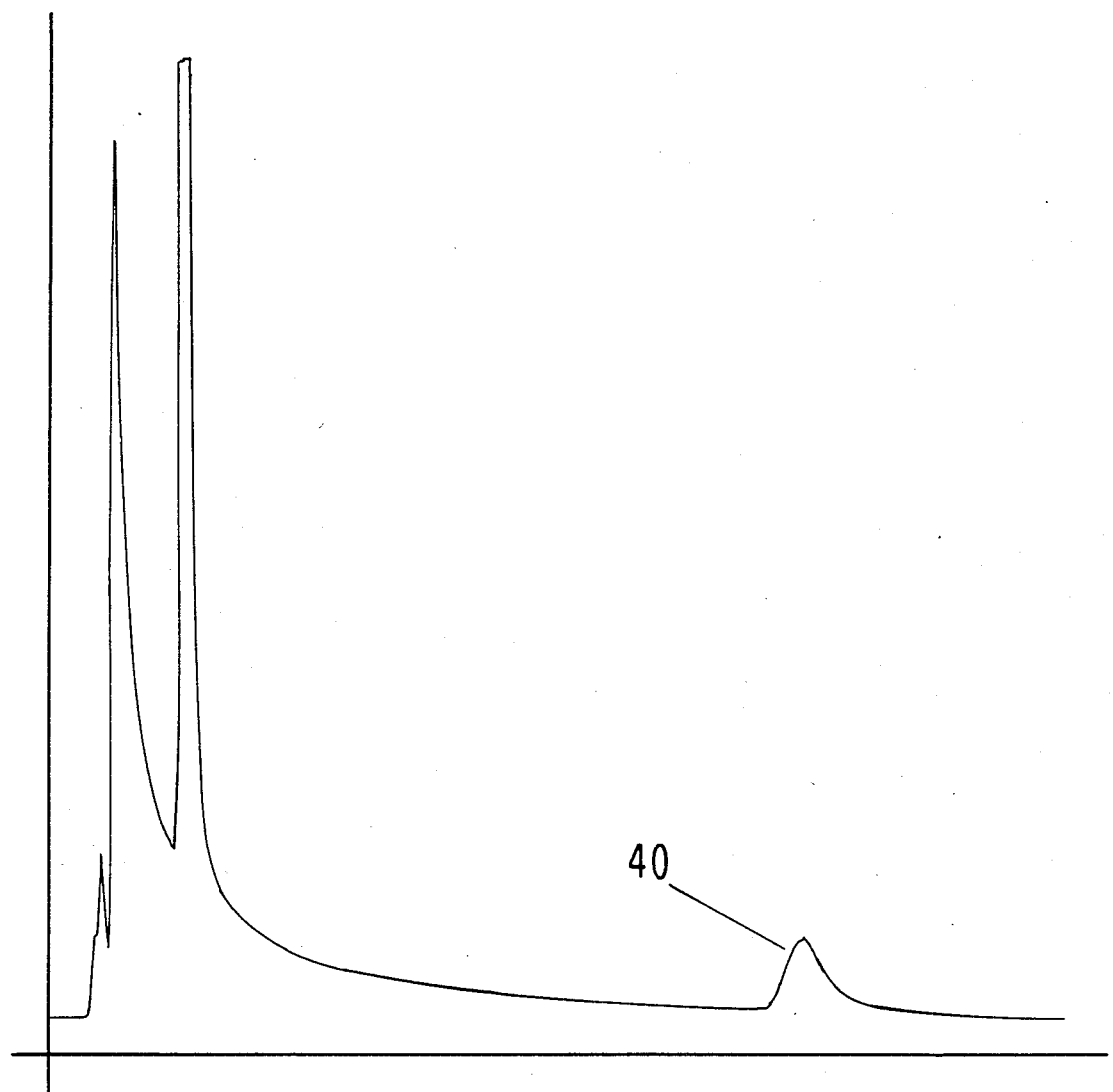

FIG. 4 is the GLC profile for the crude reaction product of Example II containing the compound having the structure:

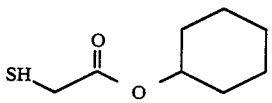

(Conditions: 8'×0.125" SE-30 column programmed at 100°–220° C. at 8° C. per minute).

FIG. 5 is the NMR spectrum for the compound having the structure:

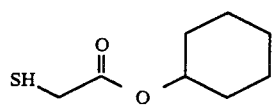

prepared according to Example II (Conditions: Field strength: 100 MHz; Solvent: CFCl₃).

Figure 6:
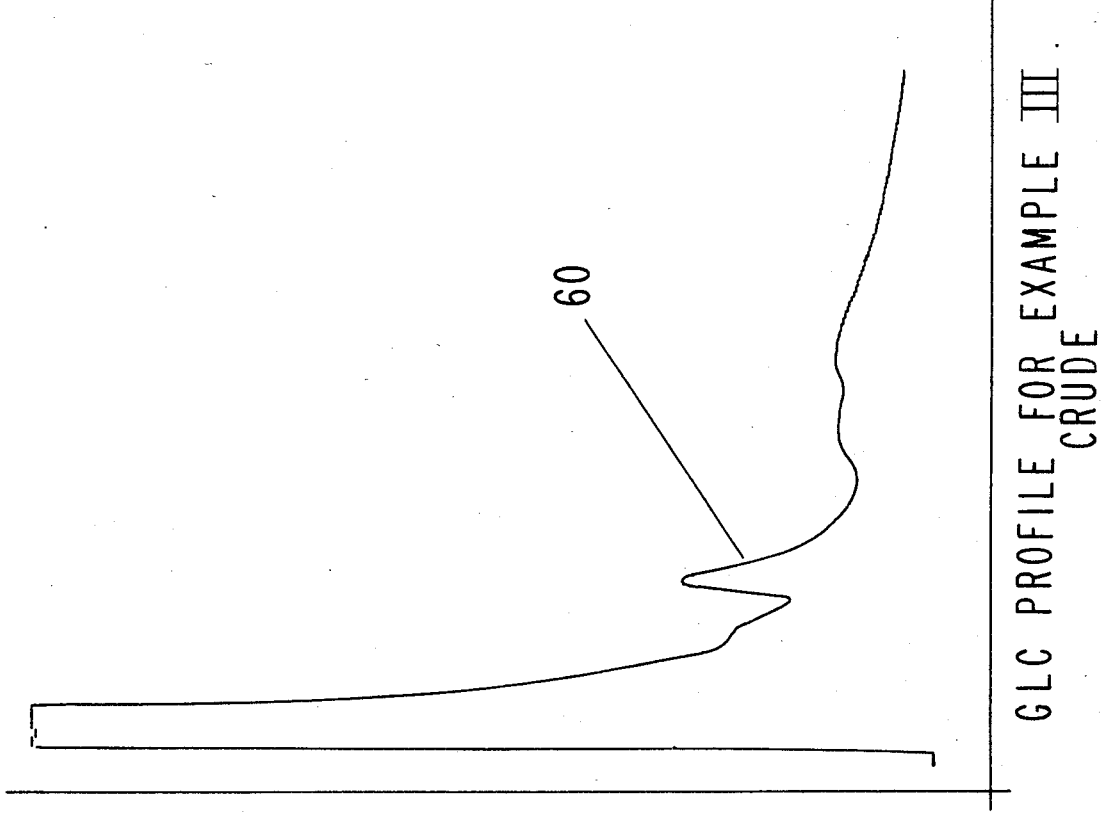

FIG. 6 is the GLC profile for the crude reaction product of Example III containing the compound having the structure:

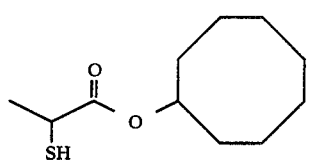

(Conditions: Carbowax column programmed at 220° C. isothermal).

FIG. 7 is the NMR spectrum for the compound having the structure:

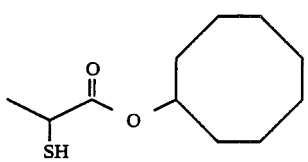

prepared according to Example III (Conditions: Field strength: 100 MHz; Solvent: CFCl₃).

FIG. 8 is the NMR spectrum for the compound having the structure:

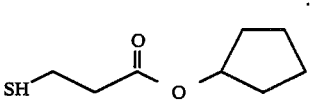

prepared according to Example IV(A) (Conditions: Field strength: 100 MHz; Solvent: CFCl₃).

Figure 9:
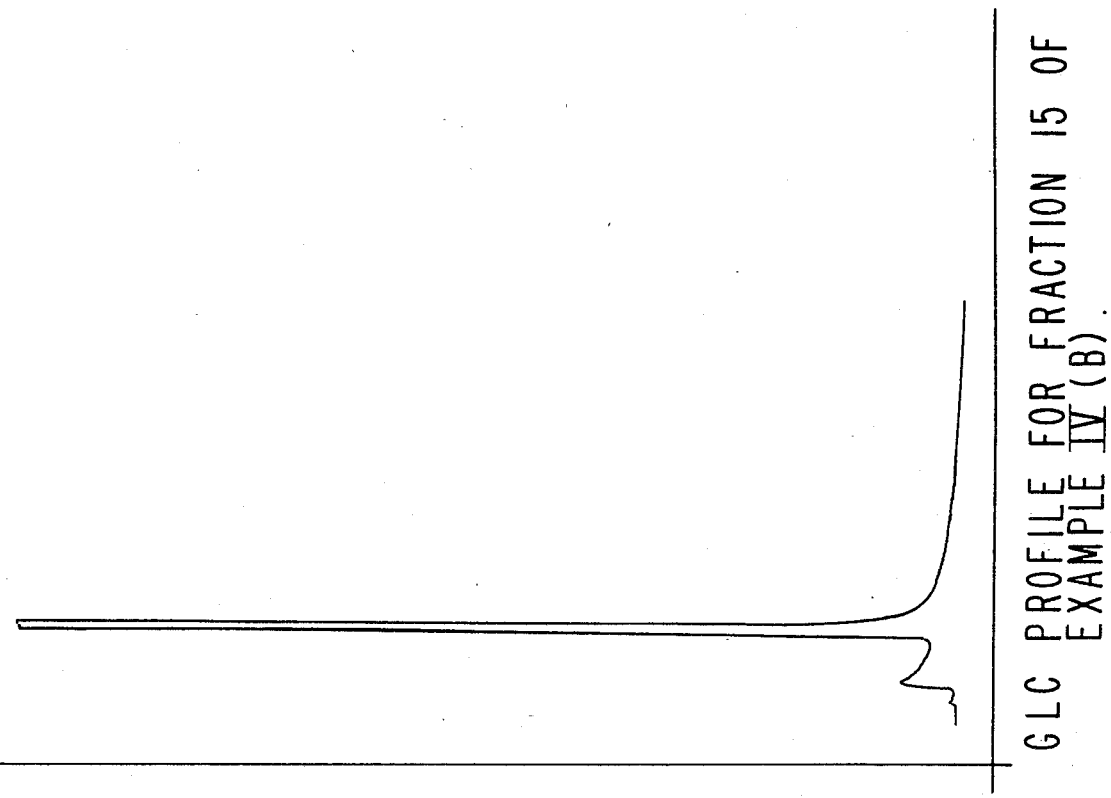

FIG. 9 is the GLC profile for Fraction 15 of the distillation product of the reaction product of Example IV(B) containing the compound having the structure:

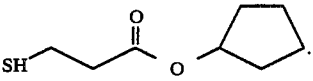

Figure 10:
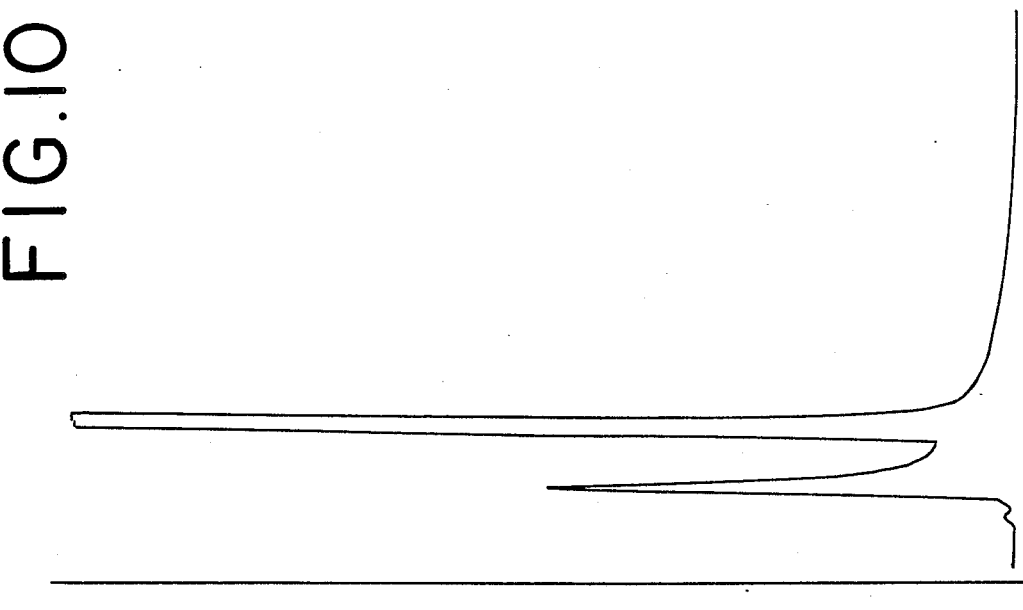

FIG. 10 is the GLC profile for Fraction 8 of the distillation product of the reaction product of Example IV(B) containing the compound having the structure:

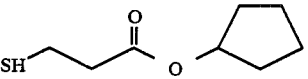

(Conditions: 8'×0.125" SE-30 column programmed at 220° C. isothermal).

Figure 11:
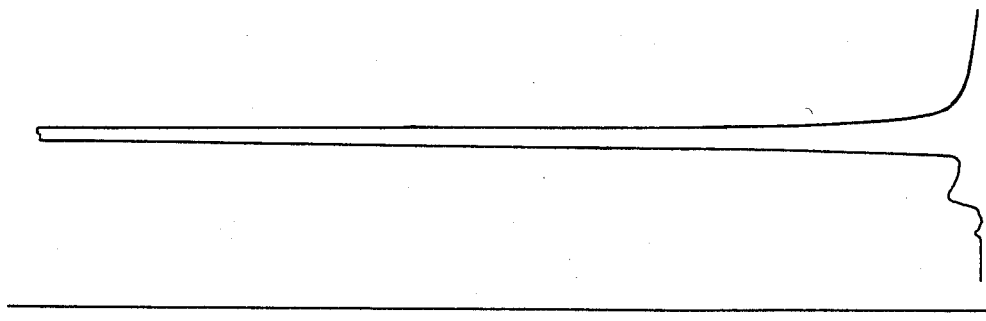

FIG. 11 is the GLC profile for Fraction 16 of the distillation product of the reaction product of Example IV(B) containing the compound having the structure:

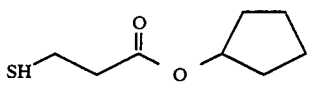

(Conditions: 8'×0.125" SE-30 column programmed at 220° C. isothermal).

FIG. 12 is the GLC profile for the crude reaction product of Example V containing the compound having the structure:

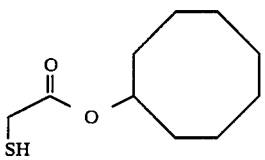

(Conditions: 8'×0.125" SE-30 column programmed at 220° C. isothermal).

FIG. 13 is the NMR spectrum for the compound having the structure:

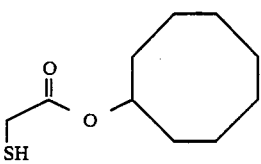

prepared according to Example V (Conditions: Field strength: 100 MHz; Solvent: CFCl₃).

Figure 14:
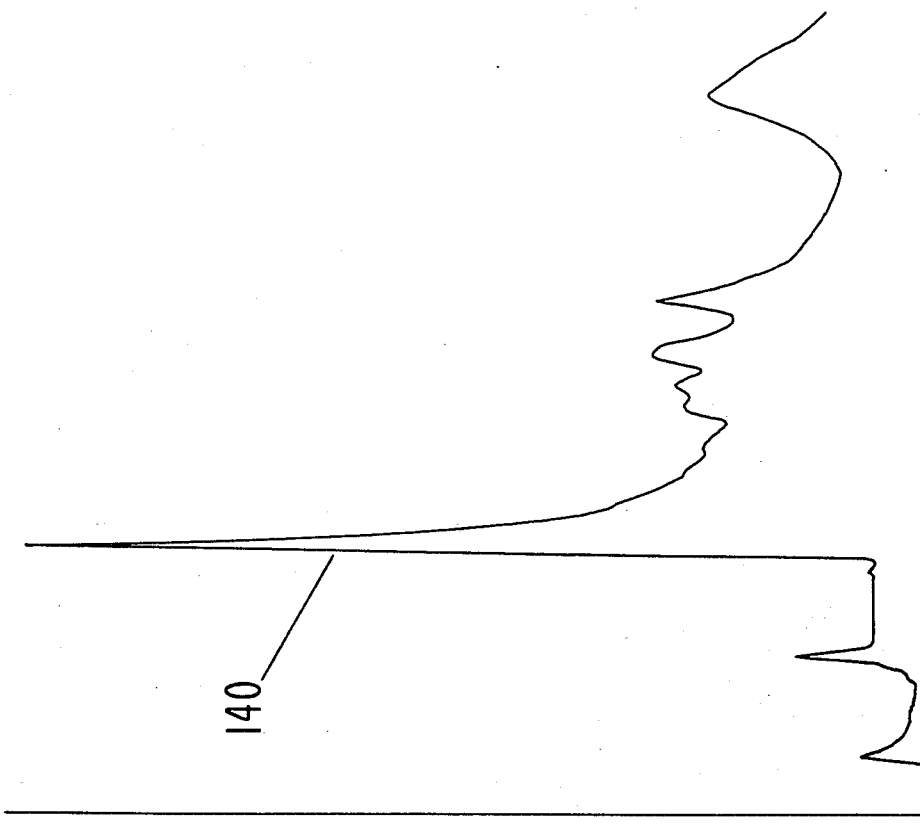

FIG. 14 is the GLC profile for the crude reaction product of Example VI containing the compound having the structure:

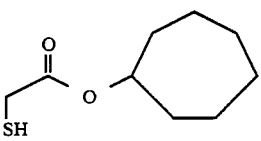

(Conditions: 8'×0.125" SE-30 column programmed at 100°–220° C. at 8° C. per minute).

FIG. 15 is the NMR spectrum for the compound having the structure:

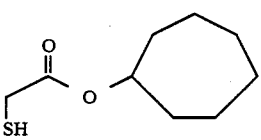

prepared according to Example VI (Conditions: Field strength: 100 MHz; Solvent: CFCl₃).

FIG. 16 is the NMR spectrum for the compound having the structure:

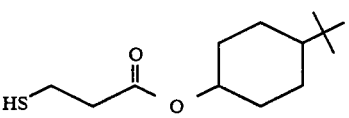

prepared according to Example VII (Conditions: Field strength: 100 MHz; Solvent: CFCl₃).

Figure 17:
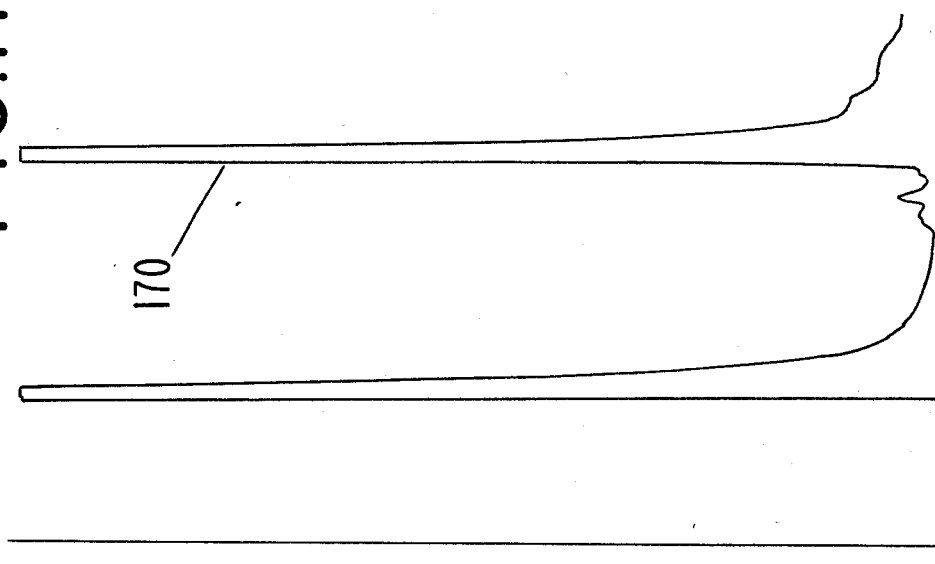

FIG. 17 is the GLC profile for the crude reaction product of Example VIII containing the compound having the structure:

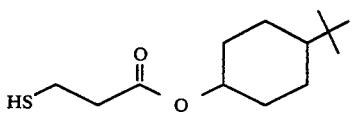

prepared according to Example VIII (Conditions: 8'×0.125" SE-30 column programmed at 100°–220° C. at 8° C. per minute).

FIG. 18 is the NMR spectrum for the compound having the structure:

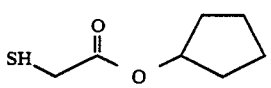

prepared according to Example VIII (Conditions: Field strength: 100 MHz; Solvent; CFCl₃).

Figure 19:
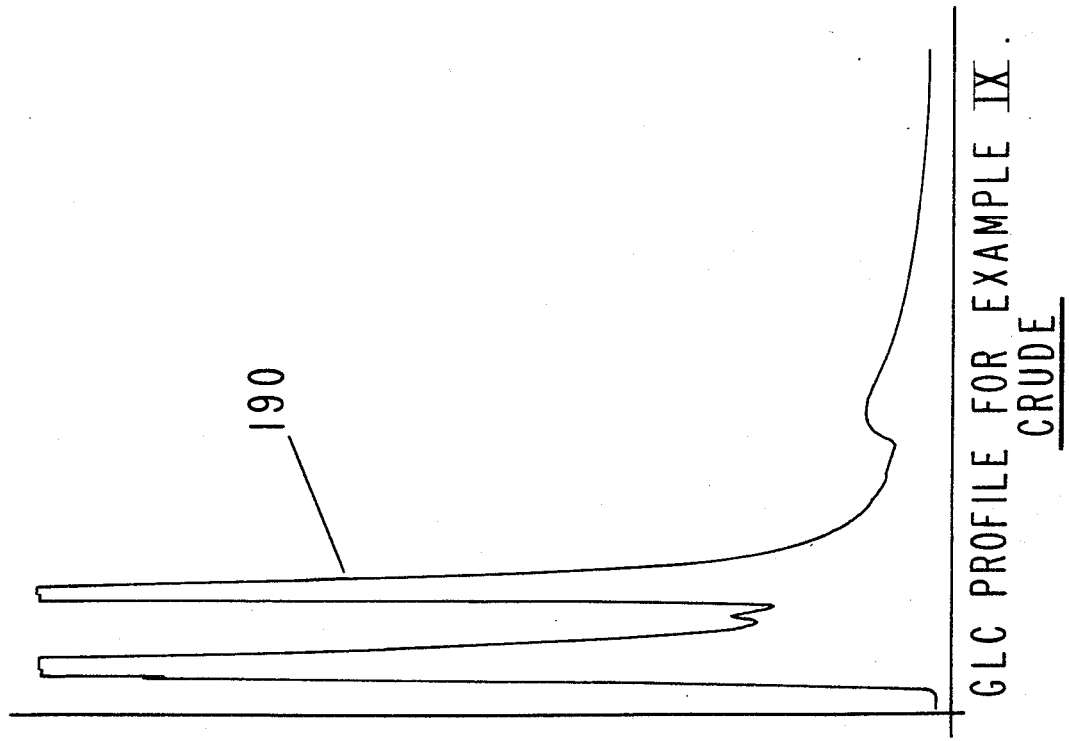

FIG. 19 is the GLC profile for the crude reaction product of Example IX contaning the compound having the structure:

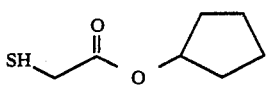

(Conditions: 8'×0.25" carbowax column programmed at 220° C. isothermal).

Figure 20:
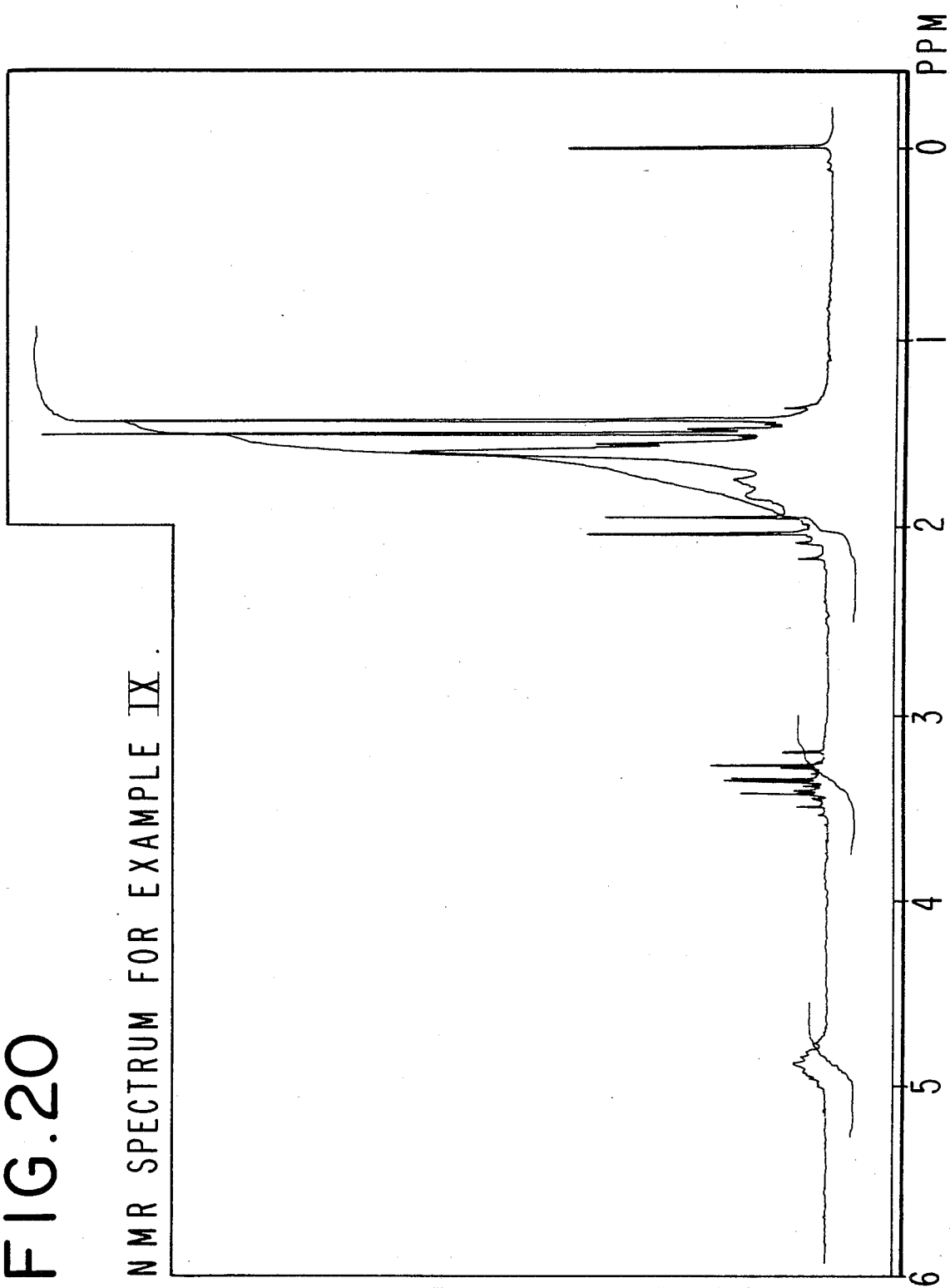

FIG. 20 is the NMR spectrum for the compound having the structure:

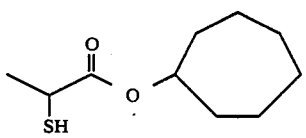

prepared according to Example IX (Conditions: Field strength: 100 MHz; Solvent: CFCl₃).

Figure 21:
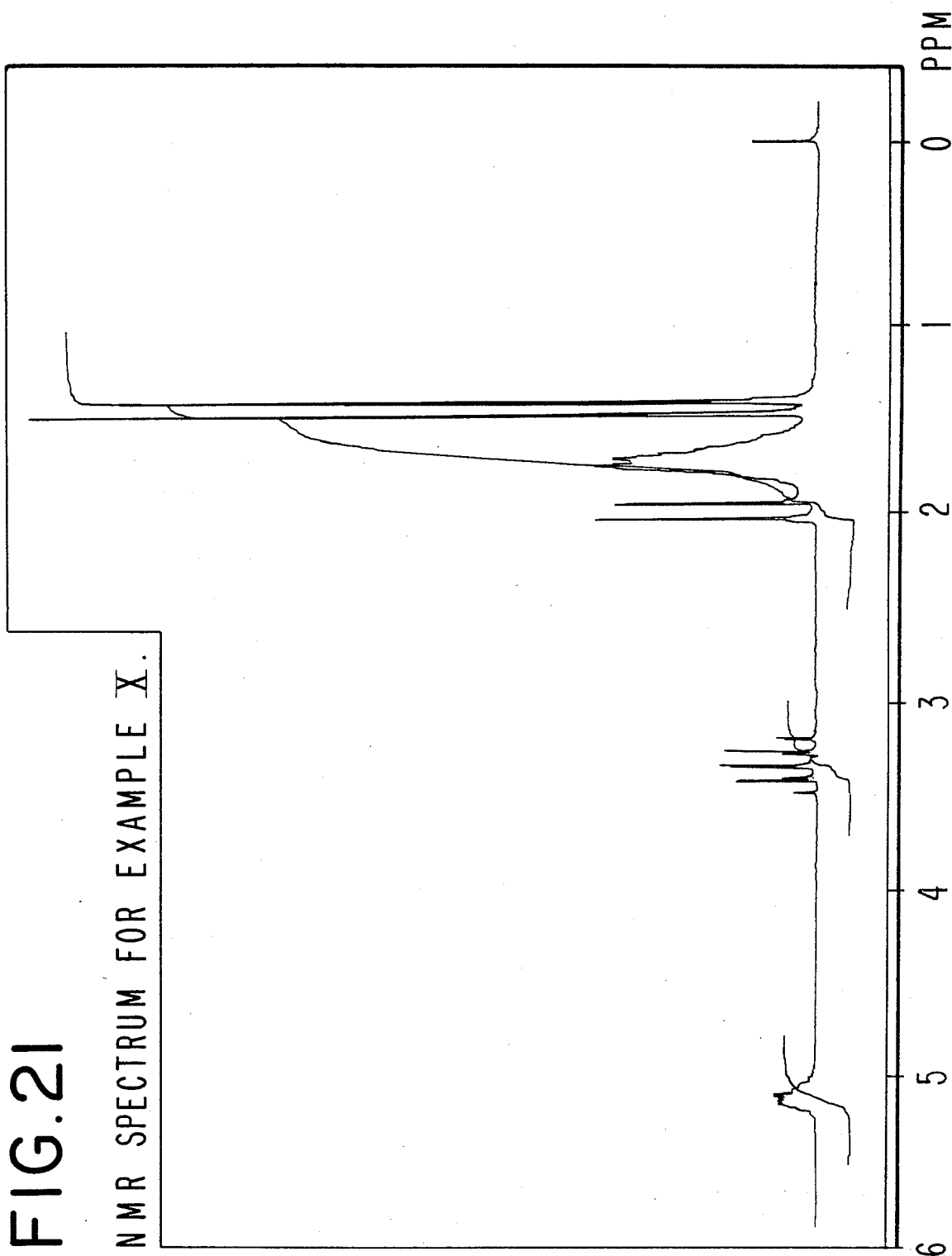

FIG. 21 is the NMR spectrum for the compound having the structure:

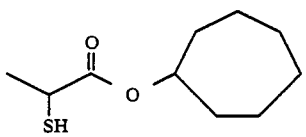

prepared according to Example X (Conditions: Field strength: 100 MHz; Solvent: CFCl₃).

Figure 22:
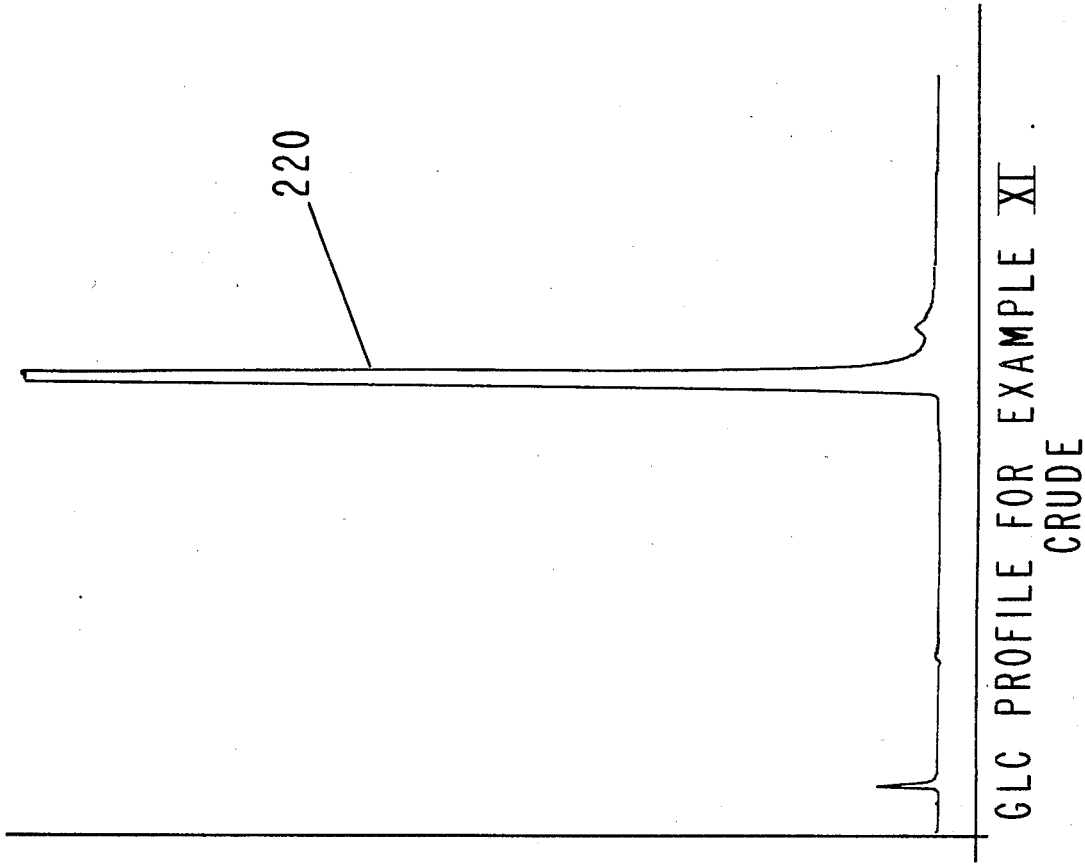

FIG. 22 is the GLC profile for the crude reaction product of Example XI containing the compound having the structure:

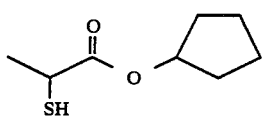

(Conditions: Carbowax column programmed at 100°–220° C. at 8° C. per minute).

FIG. 23 is the NMR spectrum for the compound having the structure:

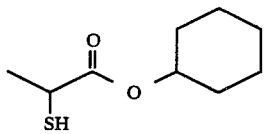

prepared according to Example XI (Conditions: Field strength: 100 MHz; Solvent: CFCl₃).

Figure 24:
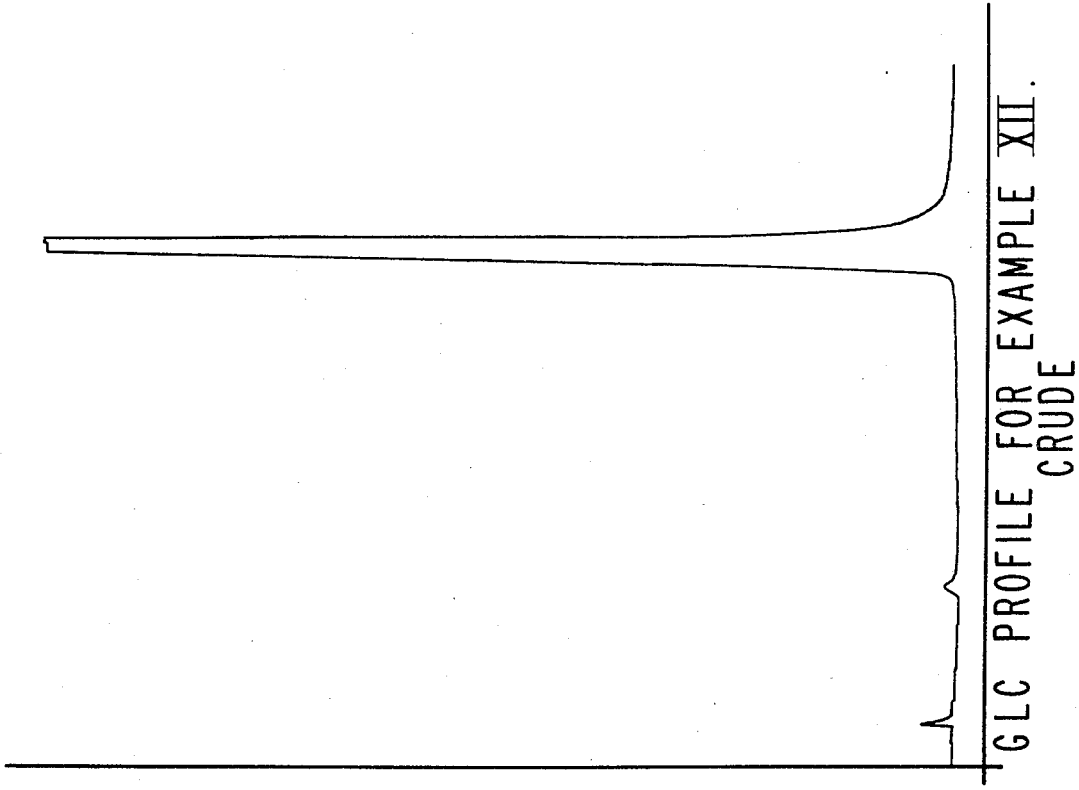

FIG. 24 is the GLC profile for the crude reaction product having the structure:

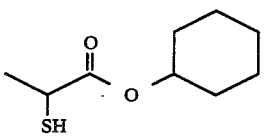

prepared according to Example XII.

Figure 25:

FIG. 25 is the NMR spectrum for the compound having the structure:

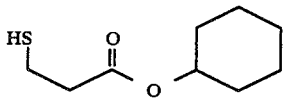

prepared according to Example XII (Conditions: Field strength: 100 MHz; Solvent: CFCl₃).

Figure 26:

FIG. 26 is the NMR spectrum for the compound having the structure:

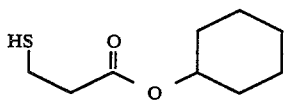

prepared according to Example XIII (Conditions: Field strength: 100 MHz; Solvent: CFCl₃).

Figure 27:
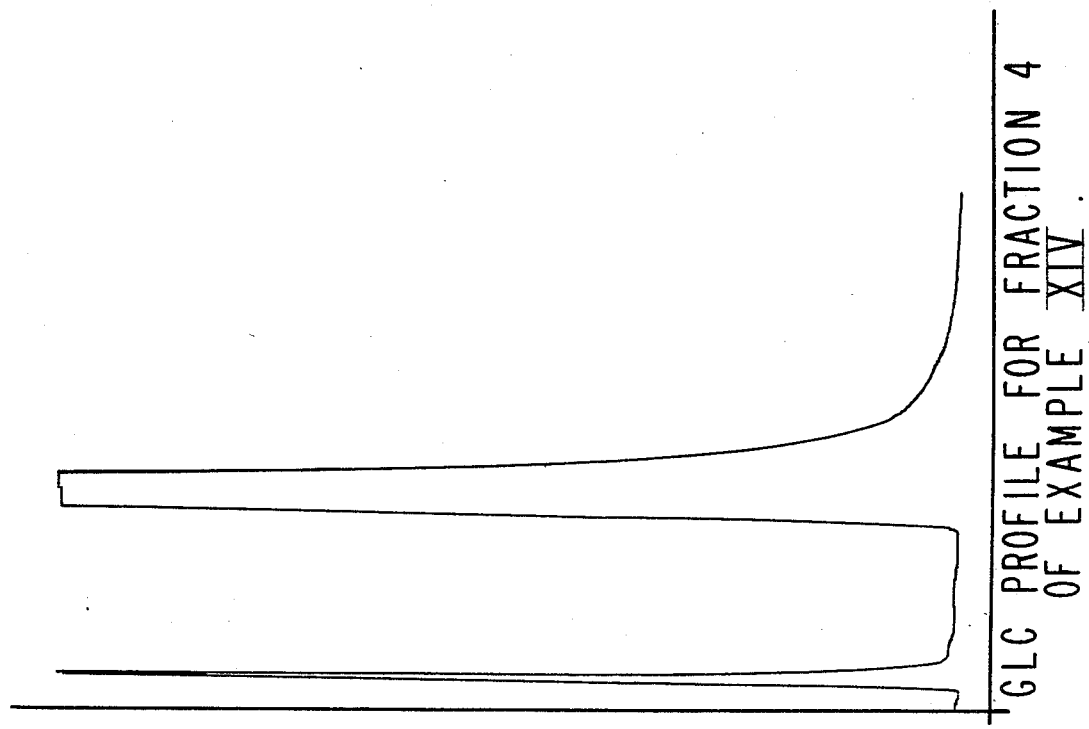

FIG. 27 is the GLC profile for Fraction 4 of the distillation product of the reaction product of Example XIV containing the compound having the structure:

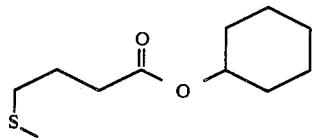

(Conditions: 8'×0.25" carbowax column programmed at 220° C. isothermal).

FIG. 28 is the GLC profile for Fraction 3 of the distillation product of the reaction product of Example XIV containing the compound having the structure:

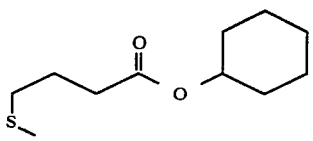

(Conditions: 8'×0.25" carbowax column programmed at 220° C. isothermal).

FIG. 29 is the NMR spectrum for Fraction 3 of the distillation product of the reaction product of Example XIV containing the compound having the structure:

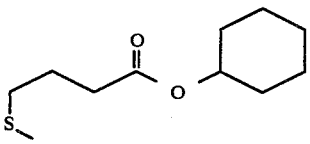

(Conditions: Field strength: 100 MHz; Solvent: CFCl₃).

FIG. 30 is the NMR spectrum for the compound having the structure:

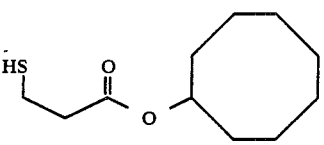

prepared according to Example XV (Conditions: Field strength: 100 MHz; Solvent: CFCl₃).

Figure 31:
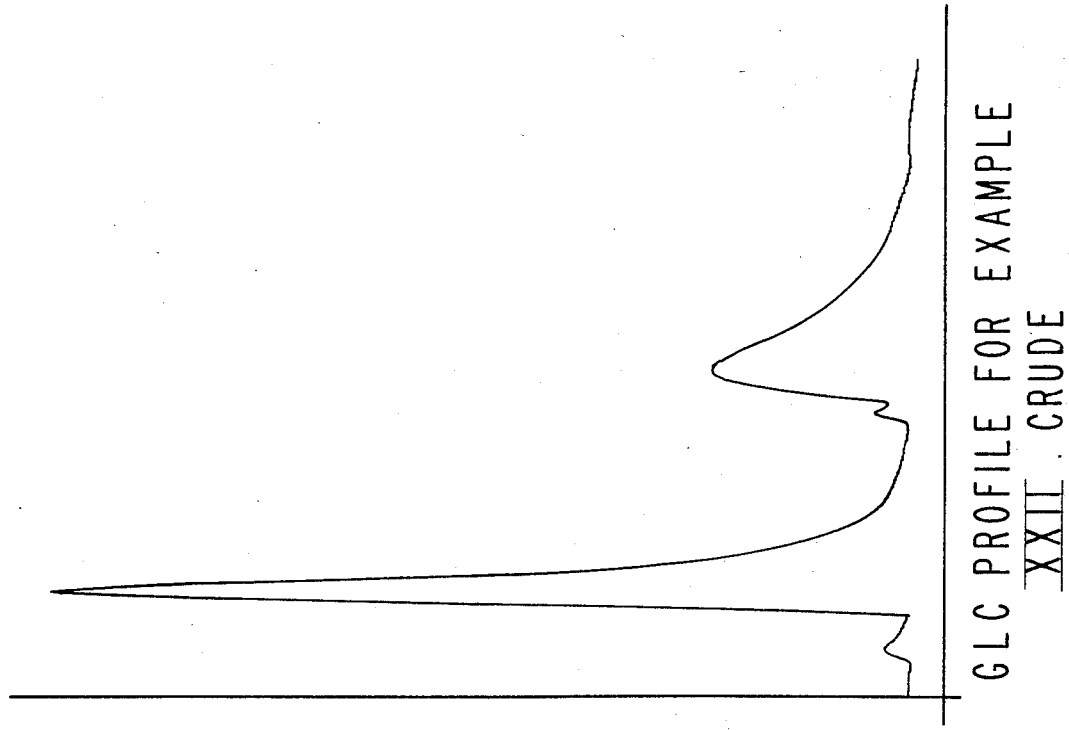

FIG. 31 is the GLC profile for the crude reaction product of Example XXII containing the compound having the structure:

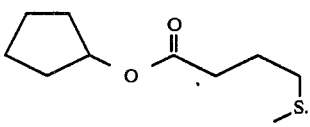

Figure 32:
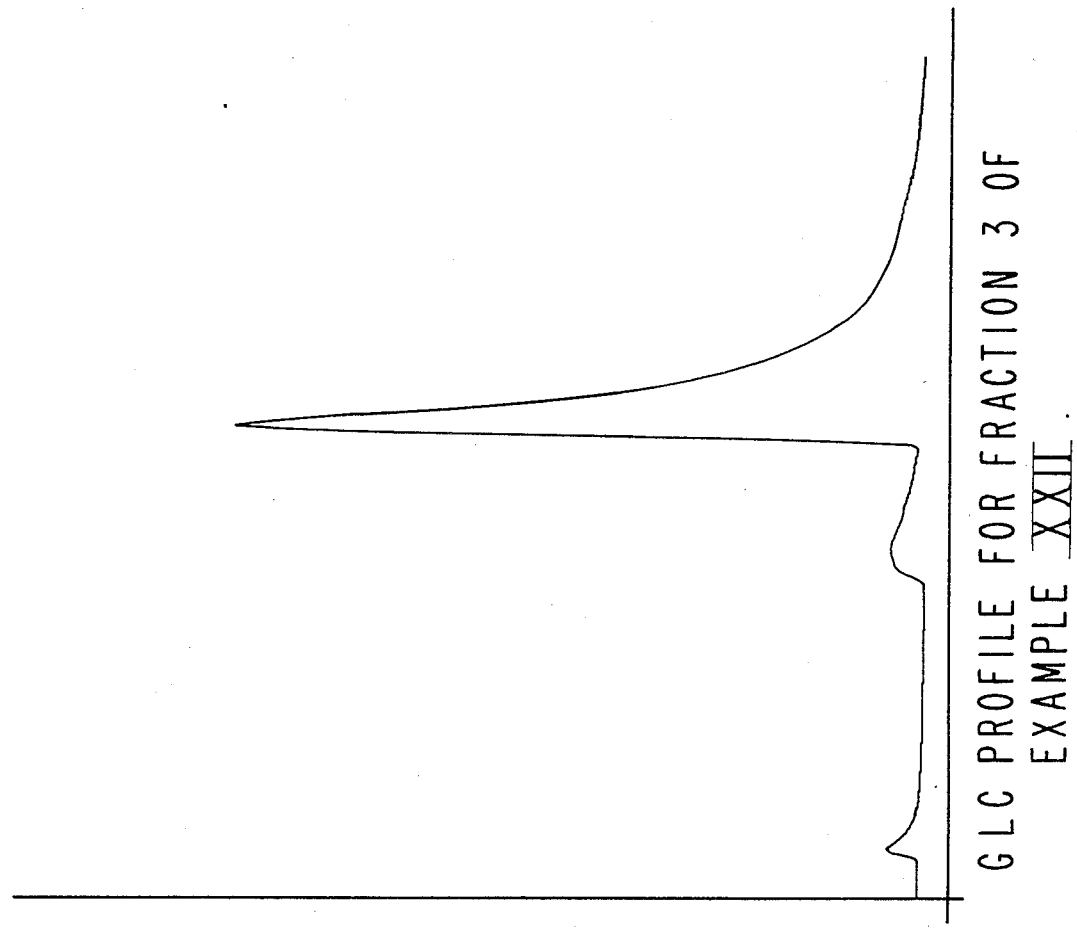

FIG. 32 is the GLC profile for Fraction 3 of the distillation of the reaction product of Example XXII containing the compound having the structure:

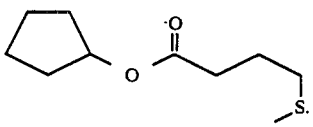

Figure 33:
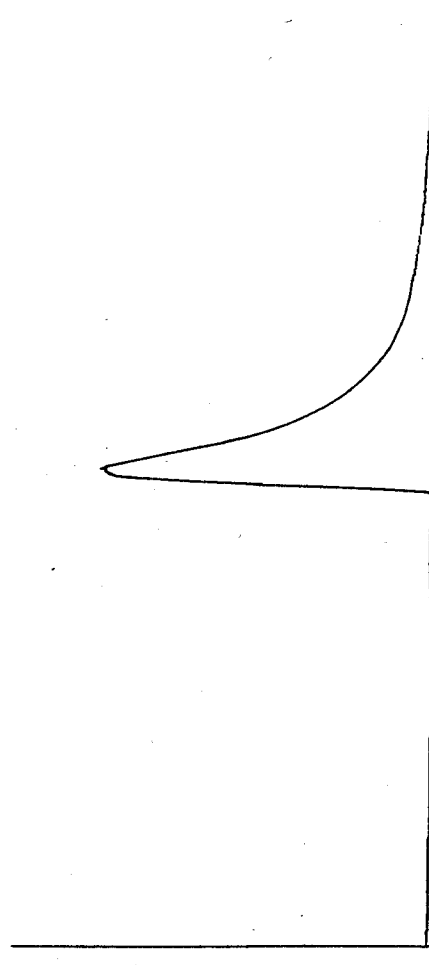

FIG. 33 is the GLC profile for Fraction 4 of the distillation of the reaction product of Example XXII containing the compound having the structure:

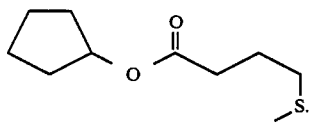

Figure 34:
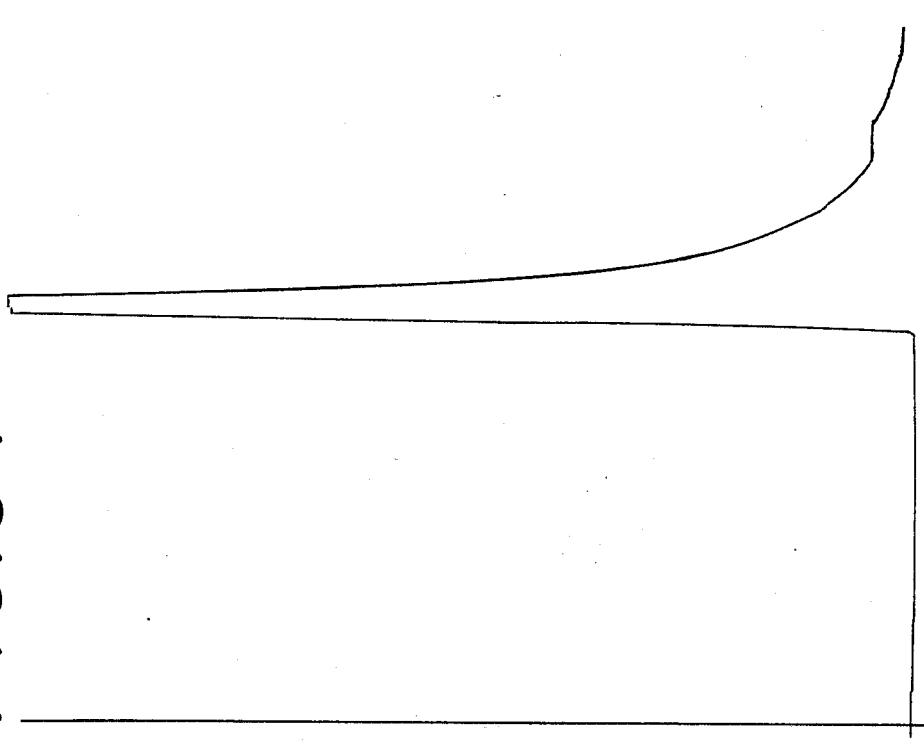

FIG. 34 is the GLC profile for Fraction 5 of the distillation of the reaction product of Example XXII containing the compound having the structure:

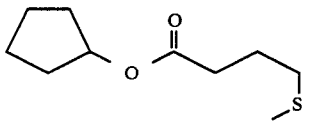

(Conditions: Carbowax column programmed at 100°-220° C. at 8° C. per minute).

FIG. 35 is the NMR spectrum for the compound having the structure:

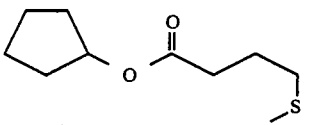

prepared according to Example XXII (Conditions: Field strength: 100 MHz; Solvent: $CFCl_3$).

Figure 36:
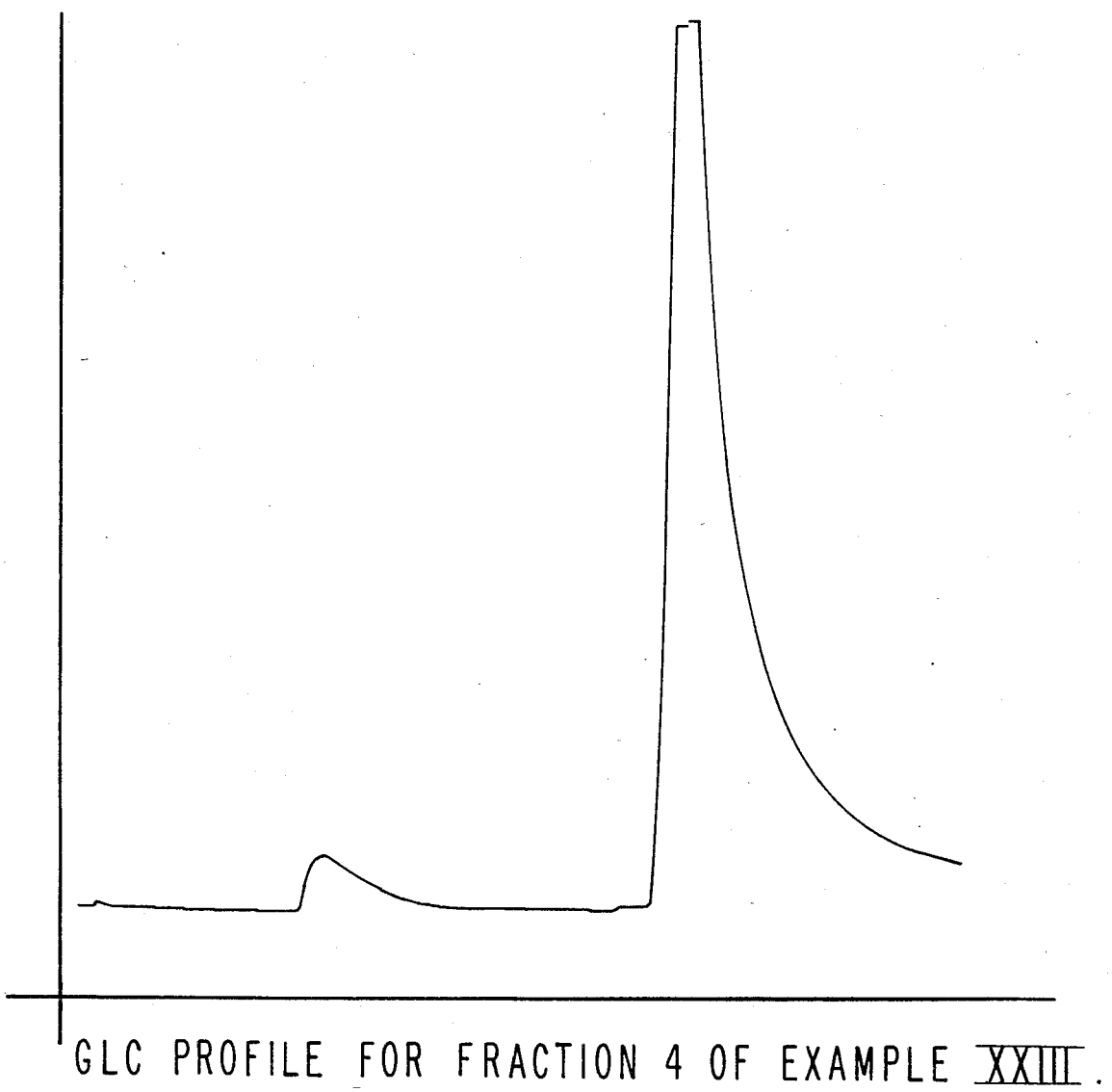

FIG. 36 is the GLC profile for Fraction 4 of the distillation of the reaction product of Example XXIII containing the compound having the structure:

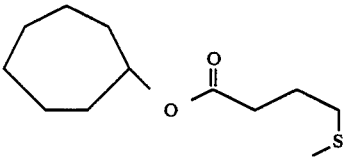

(Conditions: 8'×0.25" carbowax column programmed at 100°-220° C. at 8° C. per minute).

FIG. 37 is the NMR spectrum for Fraction 4 of the distillation of the reaction product of Example XXIII containing the compound having the structure:

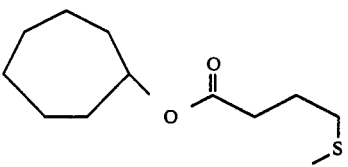

(Conditions: Field strength: 100 MHz; Solvent: $CFCl_3$).

DETAILED DESCRIPTION OF THE DRAWINGS

Figure 1:
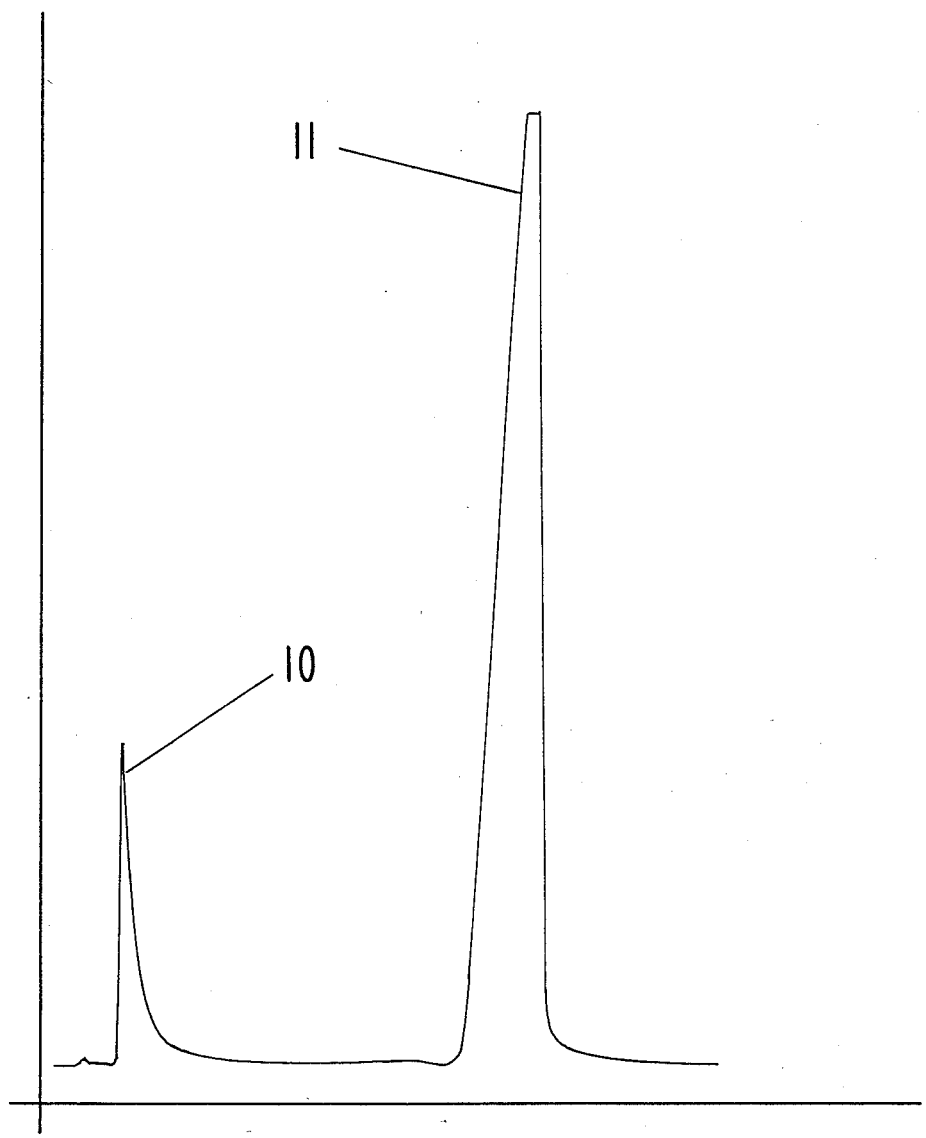
FIG. 1 is the GLC profile for the crude reaction product of Example I(A) contaning the compound having the structure.

FIG. 1 is the GLC profile for the crude reaction product of Example I(A) (Conditions: 8'×0.125" SE-30 column programmed at 220° C. isothermal). The peak indicated by reference numeral 10 is the peak for the reaction solvent. The peak indicated by reference numeral 11 is the peak for the product having the structure:

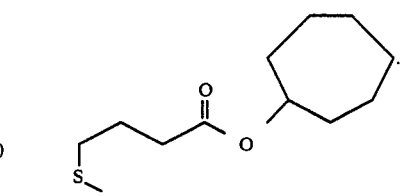

FIG. 4 is the GLC profile for the crude reaction product of Example II (Conditions: 8'×0.125" SE-30 column programmed at 100°-220° C. at 8° C. per minute). The peak indicated by reference numeral 40 is the peak for the compound having the structure:

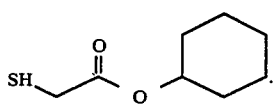

FIG. 6 is the GLC profile for the crude reaction product of Example III containing the compound having the structure:

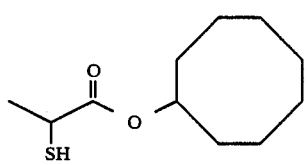

(Conditions: Carbowax column programmed at 220° C. isothermal). The peak indicated by reference numeral 60 is the peak for the compound having the structure:

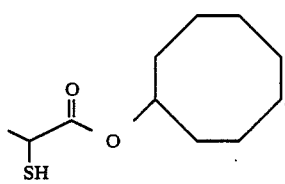

FIG. 12 is the GLC profile for the crude reaction product of Example V containing the compound having the structure:

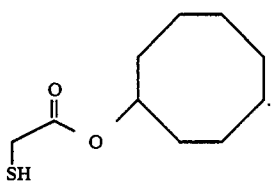

(Conditions: 8'×0.125" SE-30 column programmed at 220° C. isothermal). The peak indicated by reference numeral 120 is the peak for the compound having the structure:

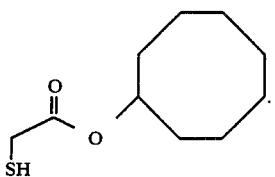

FIG. 14 is the GLC profile for the crude reaction product of Example VI containing the compound having the structure:

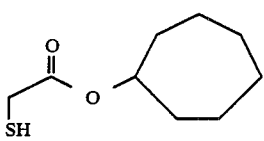

(Conditions: 8'×0.125" SE-30 column programmed at 100°-220° C. at 8° C. per minute). The peak indicated by reference numeral 140 is the peak for the compound having the structure:

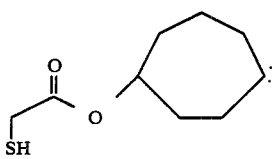

FIG. 17 is the GLC profile for the crude reaction product of Example VIII containing the compound having the structure:

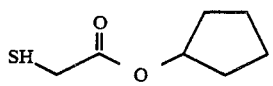

(Conditions: 8'×0.125" SE-30 column programmed at 100°-220° C. at 8° C. per minute). The peak indicated by reference numeral 170 is the peak for the compound having the structure:

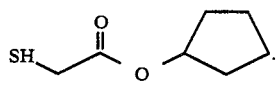

FIG. 19 is the GLC profile for the crude reaction product of Example IX containing the compound having the structure:

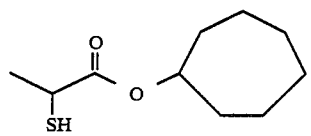

(Conditions: 8'×0.25" carbowax column programmed at 220° C. isothermal). The peak indicated by reference numeral 190 is the peak for the compound having the structure:

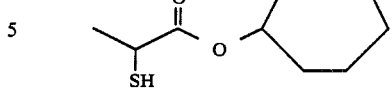

FIG. 22 is the GLC profile for the crude reaction product of Example XI containing the compound having the structure:

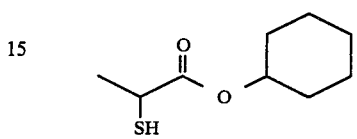

(Conditions: Carbowax column programmed at 100°-220° C. at 8° C. per minute). The peak indicated by reference numeral 220 is the peak for the the compound having the structure:

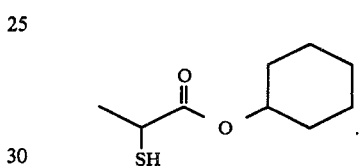

THE INVENTION

The present invention provides cycloalkyl esters of mercaptoalkanoic acids useful for augmenting or enhancing the aroma or taste of foodstuffs, said cycloalkyl esters of mercaptoalkanoic acids being defined according to the structure:

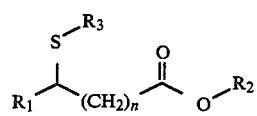

wherein $R_1$ represents hydrogen or methyl; $R_2$ represents mono $C_1$-$C_4$ alkyl substituted or unsubstituted $C_5$-$C_8$ cycloalkyl; $R_3$ represents hydrogen or methyl; and N represents 0, 1 or 2 as well as methods for augmenting, enhancing, or modifying the organoleptic properties, e.g., taste and aroma of said foodstuffs using said cycloalkyl esters of mercaptoalkanoic acids.

The cycloalkyl esters of mercaptoalkanoic acids of our invention augment or enhance roasted, roasted sesame, roasted peanut, sulfury, concord grape, burnt potato skin, cashew juice, roasted almond, floral, roasted meat, peanut, yeasty, cashew, fruity, green, kiwi, citrus, bread crust, boiled corn, boiled bean, cooked ham, pineapple, grapefruit, meaty, sesame, oniony and roasted onion aroma and taste nuances in foodstuff flavors making them useful for augmenting or enhancing flavors for such foodstuffs as peanut, almond, sesame, potato, concord grape, cashew, roasted almond, carmel, roasted meat, roasted nut, roasted, nutty, cashew, yeast, kiwi, citrus, cooked vegetable, cooked ham, pineapple, grapefruit and durian flavored foodstuffs.

The cycloalkyl esters of mercaptoalkanoic acids of our invention may be prepared by reacting an alcohol having the structure:

with a mercapto alkanoic acid having the structure:

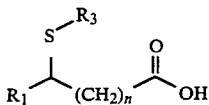

in the presence of a protonic acid such as para-toluene sulfonic acid or in the absence of such acid at temperatures in the range of from about 100° C. up to about 150°; preferably at reflux conditions at atmospheric pressure. Pressures higher than atmospheric pressure may be utilized thereby giving rise to higher temperatures of reaction and shorter time periods of reaction. The time of reaction may vary from about 3 hours up to about 15 hours depending on the temperature of reaction.

Accordingly, the reaction taking place may be shown generically, thus:

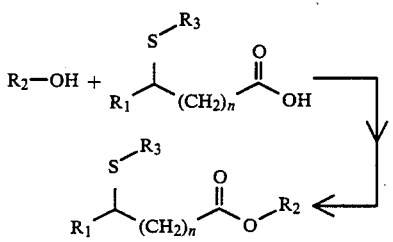

wherein $R_1$ represents hydrogen or methyl; $R_2$ represents mono $C_1$–$C_4$ alkyl substituted or unsubstituted $C_5$–$C_8$ cycloalkyl; $R_3$ represents hydrogen or methyl; and N represents 0, 1 or 2. Examples of the alcohol defined according to the structure:

are:
cyclopentanol;
cyclohexenol;
cycloheptanol;
cyclooctanol;
1-methyl cyclohexanol;
2-methyl cyclohexanol;
3-methyl cyclohexanol;
4-methyl cyclohexanol;
1-methyl cyclopentanol;
2-methyl cyclopentanol;
3-methyl cyclopentanol;
1-methyl cycloheptanol;
2-methyl cycloheptanol;
3-methyl cycloheptanol;
4-methyl cycloheptanol;
1-methyl cyclooctanol;
2-methyl cyclooctanol;
3-methyl cyclooctanol;
4-methyl cyclooctanol;
2,4-dimethyl cyclooctanol;
2,5-dimethyl cyclooctanol;
2,4-dimethyl cycloheptanol;
2,4-dimethyl cyclohexanol;
2,5-dimethyl cyclohexanol;
2,3-dimethyl cyclohexanol.

Examples of mercapto alkanoic acids defined according to the generic structure:

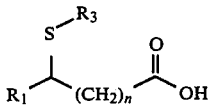

are as follows:
2-Mercapto propionic acid having the structure:

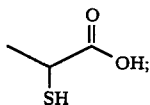

3-Mercapto propionic acid having the structure;

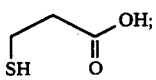

2-Mercapto acetic acid having the structure:

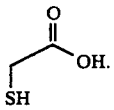

The cycloalkyl esters of mercaptoalkanoic acids of our invention may be prepared, in the alternative, by reacting a mercaptan having the structure:

wherein $R_3'$ represents $C_1$–$C_3$ lower alkyl with an alpha, beta, or gamma halogen-substituted alkanoic acid ester having the structure:

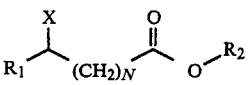

wherein $R_1$, $R_2$ and N are defined, supra and X represents chloro or bromo according to the reaction:

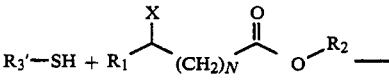

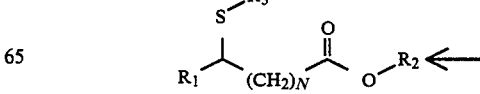

The reaction with the mercaptan having the structure:

R₃'—SH takes place in the presence of an alkali metal alkoxide catalyst such as sodium methoxide, potassium methoxide, potassium iso-t-butoxide and the like. The reaction takes place at a temperature in the range of from about 0° C. up to about 30° C. When methyl mercaptan is used as a reactant, the methyl mercaptan being a gas at room temperature and pressure is bubbled in below the reaction mass and the temperature is preferably maintained at 10°–15° C.

The cycloalkyl esters of mercaptoalkanoic acids of our invention may also be prepared by means of a reaction well known to those having ordinary skill in the art as "ester interchange" whereby a lower alkyl ester of a mercapto or alkyl mercapto alkanoic acid is reacted with a cycloalkanol, e.g., cyclohexanol, cyclopentanol, cyclooctanol, cycloheptanol or 4-t-butyl cyclohexanol according to the reaction:

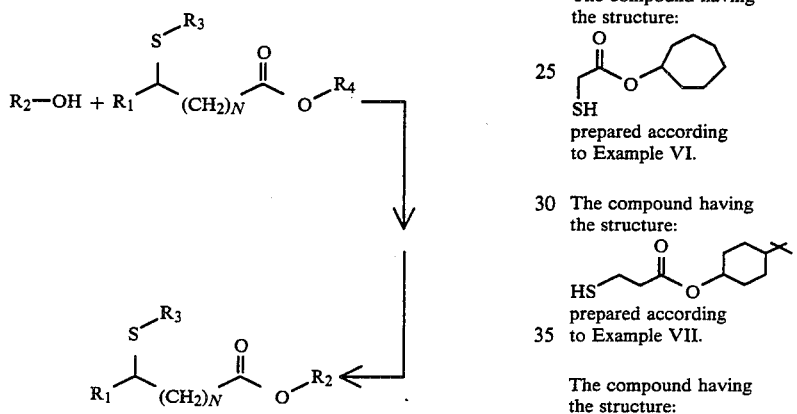

wherein $R_4$ of the molecule:

is $C_1$–$C_3$ lower alkyl, e.g., methyl, ethyl, n-propyl or isopropyl. This reaction takes place in the presence of an alkali metal alkoxide catalyst such as sodium methoxide, potassium ethoxide or potassium iso-t-butoxide at a temperature in the range of from about 90° C. up to about 130° C. at atmospheric pressure.

Examples of the products of our invention and their organoleptic properties are set forth in Table I below as follows:

TABLE I

| Structure of Compound And Example Set Forth Infra Used To Prepare Same: | Organoleptic Properties |
|---|---|
| The compound having the structure: HS–⟨⟩–C(O)–O–cyclohexyl prepared according to Example XII. | A roasted, roasted sesame and roasted peanut aroma and taste profile at 0.1 ppm causing it to be useful in peanut, almond and sesame flavored foodstuffs. |

TABLE I-continued

| Structure of Compound And Example Set Forth Infra Used To Prepare Same: | Organoleptic Properties |
|---|---|
| The compound having the structure: HS–CH₂–C(O)–O–cycloheptyl prepared according to Example XV. | A roasted, sulfury, concord grape and burnt potato skin aroma and taste profile at 0.1 ppm causing it to be useful in potato and concord grape flavored foodstuffs. |
| The compound having the structure: SH–CH–C(O)–O–cycloheptyl prepared according to Example XIII. | A roasted, cashew juice, sulfury and roasted almond aroma and taste profile at 0.01 ppm causing it to be useful in cashew juice, roasted almond and caramel flavored foodstuffs. |
| The compound having the structure: (SH)–CH–C(O)–O–cycloheptyl prepared according to Example VI. | A roasted, sulfury and floral aroma and taste profile at 0.5 ppm. |
| The compound having the structure: HS–CH₂–C(O)–O–(4-t-butylcyclohexyl) prepared according to Example VII. | A roasted and roasted meat aroma and taste profile at 0.001 ppm causing it to be useful in roasted meat, roasted nut and caramel flavored foodstuffs. |
| The compound having the structure: SH–CH–C(O)–O–cyclopentyl (GLC trap) prepared according to Example IV(A). | A roasted, peanut, yeasty and cashew aroma and taste profile at 0.1 ppm causing it to be useful in roasted, nutty, cashew and yeast flavored foodstuffs. |
| The compound having the structure: SH–CH–C(O)–O–cyclopentyl prepared according to Example IV(B), (distillation fraction bulking). | A roasted, bread crust-like, cashew juice, roasted almond, roasted sesame and concord grape aroma and taste profile at 0.2 ppm causing it to be useful in roasted almond, caramel and concord grape flavored foodstuffs. |
| The compound having the structure: (SH)–CH–C(O)–O–cycloheptyl prepared according to Example IX. | A roasted, fruity, green, Kiwi-like and citrus aroma and taste profile at 0.1 ppm causing it to be useful in Kiwi, cashew and citrus flavored foodstuffs. |
| The compound having the structure: (SH)–CH–C(O)–O–cyclopentyl prepared according to Example X. | A boiled corn, boiled green bean and cooked ham aroma and taste profile at 1 ppm. |

TABLE I-continued

| Structure of Compound And Example Set Forth Infra Used To Prepare Same: | Organoleptic Properties |
|---|---|
| The compound having the structure:<br>![structure with O, SH, O, cyclohexyl]<br>prepared according to Example XI. | A boiled corn, boiled green bean and cooked ham aroma and taste profile at 1 ppm. |
| The compound having the structure:<br>![structure with O, S, cyclohexyl ester]<br>prepared according to Example XIV. | A pineapple and green aroma and taste profile at 0.2 ppm causing it to be useful in pineapple flavored foodstuffs. |
| The compound having the structure:<br>![structure with O, S, cyclohexyl ester]<br>prepared according to Examples I(A) and I(B). | A fruity, pineapple and roasted aroma and taste profile at 0.2 ppm causing it to be useful in pineapple and peanut flavored foodstuffs. |
| The compound having the structure:<br>![SH-CH2-C(O)-O-cyclohexyl]<br>prepared according to Example II. | A roasted, roasted nut, floral, citrus and grapefruit aroma and taste profile at 0.1 ppm causing it to be useful in grapefruit and durian-flavored foodstuffs. |
| The compound having the structure:<br>![structure with O, SH, cycloheptyl ester]<br>prepared according to Example III. | A roasted, meaty and sesame aroma and taste profile at 1 ppm causing it to be useful in sesame, roasted almond and roasted peanut flavored foodstuffs. |
| The compound having the structure:<br>![SH-CH2-C(O)-O-cyclopentyl]<br>prepared according to Example VIII. | An oniony and roasted onion aroma and taste profile at 0.2 ppm. |
| The compound having the structure:<br>![structure with O, SH, cycloheptyl]<br>produced according to Example V. | A roasted, floral and grapefruit aroma and taste profile at 0.5 ppm. |
| The compound having the structure:<br>![cyclopentyl-O-C(O)-CH2CH2-S-CH3]<br>prepared according to Example XXII. | A pineapple and fruity aroma and taste profile at 5 ppm. |

At the end of the reaction as stated, supra, the reaction product is extracted from the reaction mass or the reaction mass is washed, for example, with saturated sodium chloride. The reaction product is then distilled preferably by means of vacuum distillation.

Thus, the cycloalkyl esters of mercaptoalkanoic acids of our invention can be used to alter, vary, fortify, modify, enhance or otherwise improve the organoleptic properties including flavor and/or aroma of a wide variety of materials which are ingested, consumed or otherwise organoleptically sensed.

The term "alter" in its various forms will be understood herein to mean the supplying or imparting of a flavor character or note to an otherwise bland, relatively tasteless substance or augmenting an existing flavor characteristic where the natural flavor is deficient in some regard or supplementing the existing flavor or aroma impression to modify the organoleptic character. The materials which are so altered are generally referred to herein as consumable materials.

Such cycloalkyl esters of mercaptoalkanoic acids of our invention are accordingly useful in flavoring compositions. Flavoring compositions are herein taken to mean those which contribute a part of the overall flavor impression by supplementing or fortifying a natural or artifical flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus foodstuffs include meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the cycloalkyl esters of mercaptoalkanoic acids of our invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers. Examples of preferred co-flavoring adjuvants are:

Methyl thiazole alcohol (4-methyl-5-betahydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
Alkyl pyrazine;
Methyl pyrazine;
2-Ethyl-3-methyl pyrazine;
Polysulfides;
Dipropyl disulfide;
Allyl propyl disulfide;
Allyl propyl trisulfide;
Allyl propenyl disulfide;
Allyl propenyl trisulfide;
Methyl benzyl disulfide;
Alkyl thiophenes;
2-Butyl thiophene;
2,3-Dimethyl thiophene;
5-Methyl furfural;
2,5-Dimethyl-3-acetyl furan;
2,4-Decadienal;
Guiacol;
Phenyl acetaldehyde;
Gamma-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
n-Henanal;
Diacetyl;
Monosodium glutamate;
Monopotassium glutamate;
Sulphur-containing amino acids, e.g., cysteine;
Hydrolyzed vegetable protein;
2-Methylfuran-3-thiol;
2-Methyldihydrofuran-3-thiol;
2,5-dimethylfuran-3-thiol;
Hydrolyzed fish protein; and
Tetramethyl pyrazine.

The cycloalkyl esters of mercaptoalkanoic acids or the compositions incorporating them, as mentioned above, can be combined with one or more vehicles or carriers for adding them to the particular product to be flavored. Vehicles can be edible or otherwise suitable materials such as ethyl alcohol, propylene glycol, water and the like. Carriers include materials such as gum arabic, carrageenan, guar gum, xantham gum and the like. The cycloalkyl esters of mercaptoalkanoic acids of our invention can be incorporated with the carriers by conventional means such as spray-drying, drum-drying and the like. Such carriers can also include materials for coacervating the cycloalkyl esters of mercaptoalkanoic acids of our invention (and other flavoring ingredients, as present) to provide encapsulated products. When the carrier is an emulsion, the flavoring composition can also contain emulsifiers such as mono- and diglycerides or fatty acids and the like. With these carriers or vehicles, the desired physical form of the composition can be prepared.

The quantity of cycloalkyl esters of mercaptoalkanoic acids utilized should be sufficient to impart the desired flavor characteristics to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subject; and the preconsumption treatment, such as baking, frying and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.001 parts per million (ppm) to about 250 ppm of cycloalkyl esters of mercaptoalkanoic acids or mixtures thereof. More particularly, in food compositions it is desirable to use from about 0.001 ppm to 100 ppm for enhancing flavors and in certain preferred embodiments of the invention, from about 0.001 to 50 ppm of the derivatives are included to add positive flavors to the finished product.

The amount of cycloalkyl esters of mercaptoalkanoic acids or mixtures thereof of our invention to be utilized in flavoring compositions can be varied over a wide range depending upon the particular quality to be added to the foodstuff. Thus, amounts of one or more derivatives according to the present invention of from about 0.04 ppm up to 80 to 90 percent of the total flavoring composition can be incorporated in such compositions. It is generally found to be desirable to include from about 0.05 ppm up to about 0.1 percent of the cycloalkyl esters of mercaptoalkanoic acids in such compositions.

The following examples are given to illustrate embodiments of the invention as it is preferred to practice it. It will be understood that these examples are illustrative and the invention is not to be considered as restricted thereto except as indicated in the appended claims.

All parts, proportions, percentages and ratios used herein are by weight unless otherwise indicated.

EXAMPLE I(A)

PREPARATION OF THE CYCLOHEPTYL ESTER OF 4-(METHYLTHIO)BUTYRIC ACID

Reaction:

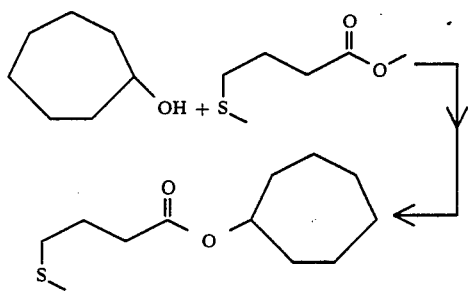

Into a 250 ml reaction flask equipped with magnetic stirrer, heating mantle, thermometer, and nitrogen sparger are placed 11.4 grams cycloheptanol; 8.1 grams of the methyl ester of 4-methylthiobutyric acid; and 0.5 grams of sodium methoxide. With stirring, the reaction mass is slowly heated to 100° C. over a 15 minute period. The reaction mass is stirred at 100° C. for a period of 5 hours. At the end of the 5 hour period, the reaction mass is washed with saturated sodium chloride, dried over anhydrous magnesium sulfate and fractionally distilled yielding the following fractions:

| Fraction No. | Vapor Temp. (°C.) | Liquid Temp. (°C.) | Vacuum mm/Hg. Pressure |
|---|---|---|---|
| 1 | 70/70 | 110/103 | 10 |
| 2 | 165 | 180 | 10 |
| 3 | 165 | 185 | 10 |
| 4 | 165 | 95 | 10 |

The resulting product has a pineapple and sulfury aroma and taste profile at 10 ppm.

FIG. 1 is the GLC profile of the crude reaction product. The peak indicated by reference numeral 10 is the peak for the excess "solvent", in this case the reactant, cycloheptanol. The peak indicated by reference numeral 11 is the peak for the product having the structure:

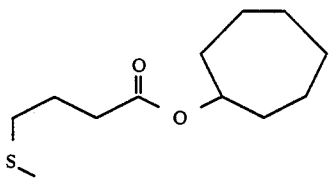

(GLC conditions: 8'×0.125" SE-30 column programmed at 220° C. isothermal).

FIG. 2 is the NMR spectrum for the compound having the structure:

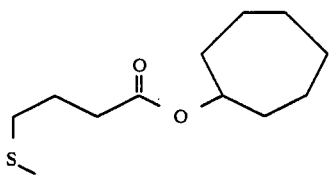

(Conditions: Field strength: 100 MHz; Solvent: CFCl₃).

EXAMPLE I(B)

PREPARATION OF THE CYCLOHEPTYL ESTER OF 4-(METHYLTHIO)BUTYRIC ACID

Reaction:

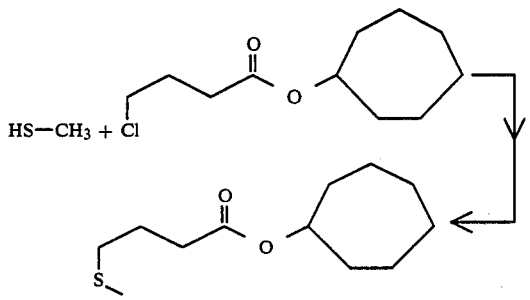

Into a 250 ml reaction flask equipped with hot plate, reflux condenser, stirring bar and gas bubbler are placed 35 grams of sodium methoxide and 25 ml of methyl alcohol. Over a period of 15 minutes, 30 grams of methyl mercaptan are added using the gas bubbler, below the surface of the reaction mixture with stirring. After the methyl mercaptan is added, with stirring 86 grams of chlorocycloheptyl butyrate is added to the reaction mass while maintaining the reaction temperature at 10°-15° C. The reaction mass is continued to be stirred for a period of 8 hours at 10°-15° C.

At the end of the reaction, the reaction mass is transferred to a separatory funnel and washed with three 100 ml volumes of water followed by drying over anhydrous sodium sulfate. The reaction mass is then fractionally distilled to yield the compound having the structure:

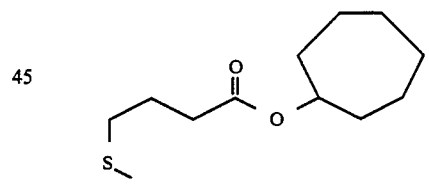

as confirmed by NMR, IR, GLC and mass spectral analyses. The reaction product having the structure:

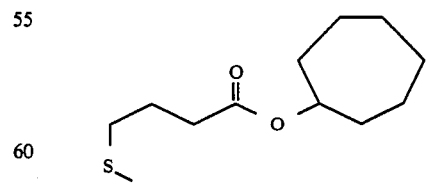

has a fruity, pineapple and roasted aroma and taste profile at 0.2 ppm causing it to be useful in pineapple and peanut-flavored foodstuffs.

FIG. 3 is the NMR spectrum for the compound having the structure:

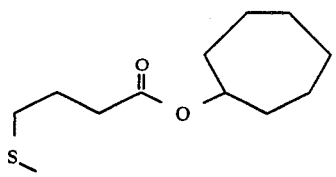

prepared according to this example (Conditions: Field strength: 100 MHz; Solvent: CFCl₃).

EXAMPLE II

PREPARATION OF CYCLOHEXYL MERCAPTO ACETATE

Reaction:

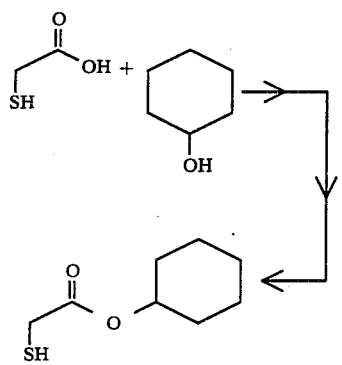

Into a 100 ml reaction flask equipped with stirrer, condenser, thermometer, hot plate, heating mantle and spin bar are placed 25 grams of cyclohexenol, 9.2 grams of mercapto acetic acid and 0.5 grams of paratoluene sulfonic acid. The reaction mass is heated to reflux and maintained at reflux for a period of 10 hours. At the end of the reaction, the reaction mass is fractionally distilled yielding the compound having the structure:

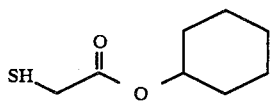

(as confirmed by NMR, IR and mass spectral analyses). The product having the structure:

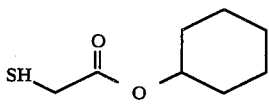

has a roasted, roasted nut, floral, citrus and grapefruit aroma and taste profile at 0.1 ppm causing it to be useful in grapefruit and durian-flavored foodstuffs.

FIG. 4 is the GLC profile for the crude reaction product containing the compound having the structure:

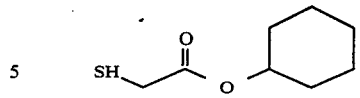

(Conditions: 8'×0.125" SE-30 column programmed at 100°-220° C. at 8° C. per minute). The peak indicated by reference numeral 40 is the peak for the compound having the structure:

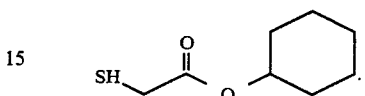

FIG. 5 is the NMR spectrum for the compound having the structure:

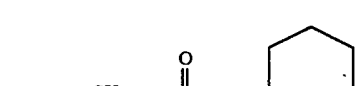

(Conditions: Field strength: 100 MHz; Solvent: CFCl₃).

EXAMPLE III

PREPARATION OF CYCLOOCTYL-2-MERCAPTOPROPIONATE

Reaction:

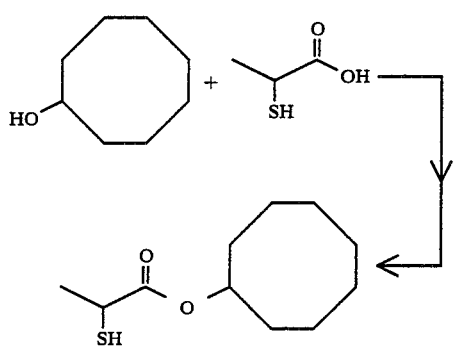

Into a 100 ml reaction flask equipped with reflux condenser, thermometer, hot plate, spin bar and heating mantle are placed 12.8 grams of cyclooctanol; 22 grams of 2-mercaptopropionic acid and 0.5 grams of paratoluene sulfonic acid. The reaction mass is heated to reflux and maintained at reflux for a period of 10 hours. At the end of the reaction mass, the reaction product is washed with one 25 ml volume of water and dried over anhydrous sodium sulfate. The reaction mass is then distilled on a micro distillation column yielding the compound having the structure:

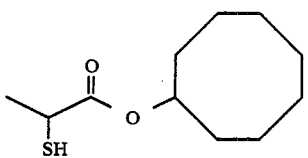

The compound having the structure:

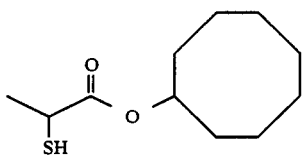

has a roasted, meaty and sesame aroma and taste profile at 1 ppm causing it to be useful in sesame, roasted almond and roasted peanut flavored foodstuffs.

FIG. 6 is the GLC profile of the crude reaction product containing the compound having the structure:

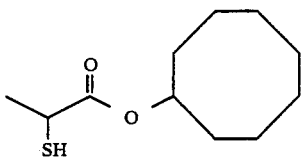

(Conditions: Carbowax column programmed at 220° C. isothermal). The peak indicated by reference numeral 60 is the peak for the compound having the structure:

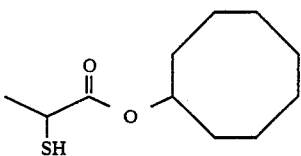

FIG. 7 is the NMR spectrum for the compound having the structure:

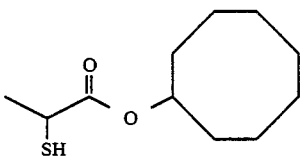

(Conditions: Field strength: 100 MHz; Solvent: CFCl₃).

EXAMPLE IV(A)

PREPARATION OF CYCLOPENTYL-3-MERCAPTOPROPIONATE

Reaction:

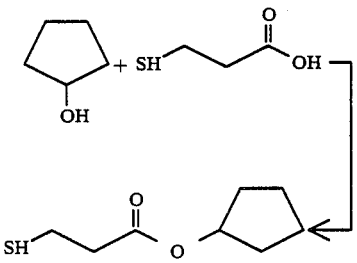

Into a 250 cc reaction flask equipped with stirrer, thermometer, reflux condenser and heating mantle are placed 100 grams of cyclopentanol; 25 grams of 3-mercaptopropionic acid and 0.5 grams of paratoluene sulfonic acid. The reaction mass is heated to reflux and maintained at reflux for a period of 8 hours. At the end of the 8 hour period, the reaction mass is admixed with 200 ml of anhydrous diethylether and then washed with two 100 ml volumes of 10% aqueous sodium carbonate followed by one 100 ml volume of water. The reaction mass is dried over anhydrous magnesium sulfate and the solvent is recovered on a Buchi evaporator. The reaction mass is then distilled using micro distillation apparatus to yield the compound having the structure:

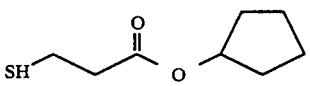

A GLC trap of this compound gives rise to a material having a roasted peanut, yeasty and cashew aroma and taste profile at 0.1 ppm causing it to be useful in roasted, nutty, cashew and yeast flavored foodstuffs.

FIG. 8 is the NMR spectrum for the compound having the structure:

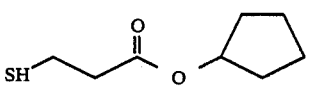

(Conditions: Field strength: 100 MHz; Solvent: CFCl₃).

EXAMPLE IV(B)

PREPARATION OF CYCLOPENTYL-3-MERCAPTOPROPIONATE

Reaction:

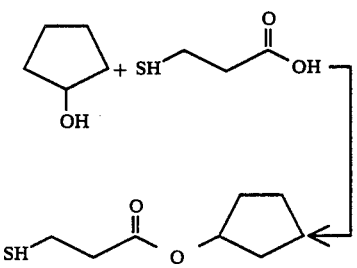

Into a 1 liter reaction flask equipped with heating mantle, stirrer, thermometer and reflux condenser are placed 172 grams of cyclopentanol; 265 grams of 3-mercaptopropionic acid and 0.5 grams of paratoluene sulfonic acid. The reaction mass is heated to reflux and reflux is continued for a period of 8 hours. At the end of the 8 hour period, the reaction mass is fractionally distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 60/ | 84/ | 4 |
| 2 | 95 | 98 | 2 |
| 3 | 97 | 55 | 2 |
| 4 | 98 | 100 | 2 |
| 5 | 99 | 100 | 2 |
| 6 | 99 | 101 | 2 |
| 7 | 99 | 102 | 2 |
| 8 | 100 | 115 | 2 |

-continued

| Fraction No. | Vapor Temp. (°C.) | Liquid Temp. (°C.) | Vacuum mm/Hg. Pressure |
|---|---|---|---|
| 9 | 110 | 160 | 2 |

Fractions 1–9 are bulked and redistilled on a one foot stone-packed column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 50/ | 115/ | 20 | 9:1 |
| 2 | 60 | 120 | 20 | 9:1 |
| 3 | 108 | 118 | 10 | 9:1 |
| 4 | 104 | 118 | 10 | 9:1 |
| 5 | 104 | 118 | 10 | 9:1 |
| 6 | 105 | 120 | 10 | 9:1 |
| 7 | 105 | 120 | 10 | 9:1 |
| 8 | 104 | 120 | 10 | 9:1 |
| 9 | 104 | 118 | 10 | 9:1 |
| 10 | 102 | 118 | 10 | 9:1 |
| 11 | 102 | 116 | 10 | 9:1 |
| 12 | 102 | 119 | 10 | 9:1 |
| 13 | 102 | 124 | 10 | 19:1 |
| 14 | 102 | 132 | 10 | 19:1 |
| 15 | 103 | 150 | 10 | 19:1 |
| 16 | 100 | 176 | 10 | 19:1 |

The resulting distillation product (bulked Fractions 8–16) has a roasted, bread crust, cashew juice, roasted almond, roasted sesame and concord grape aroma and taste profile at 0.2 ppm causing it to be useful in roasted almond, caramel and concord grape flavored foodstuffs.

GLC, IR, NMR and mass spectral analysis confirm that the product has the structure:

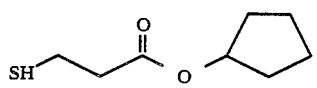

FIG. 9 is the GLC profile for Fraction 15 of the foregoing distillation.

FIG. 10 is the GLC profile for Fraction 8 of the foregoing distillation.

FIG. 11 is the GLC profile for Fraction 16 of the foregoing distillation. All GLC conditions are 8′×0.125″ SE-30 column programmed at 220° C. isothermal.

EXAMPLE V

PREPARATION OF CYCLOOCTYL MERCAPTOACETATE

Reaction:

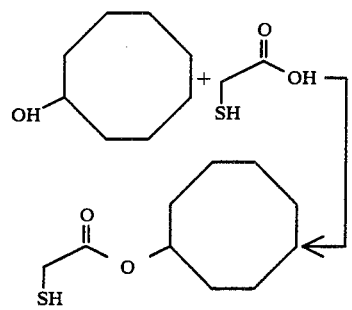

Into a 100 ml reaction flask equipped with stirrer, thermometer, reflux condenser and heating mantle are placed 32 grams of cyclooctanol; 9.2 grams of mercaptoacetic acid and 0.5 grams paratoluene sulfonic acid.

The reaction mass is heated to reflux and maintained at reflux for a period of 8 hours. At the end of the 8 hour period, the reaction mass is washed with one 25 ml volume of water and then dried over anhydrous sodium sulfate. The reaction mass is then distilled on a micro distillation apparatus yielding the compound having the structure:

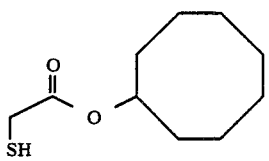

The compound having the structure:

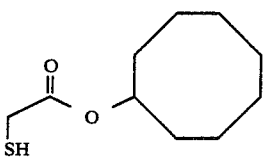

has a roasted, floral and grapefruit aroma and taste profile at 0.5 ppm.

FIG. 12 is the GLC profile for the crude reaction product (Conditions: 8′×0.125″ SE-30 column programmed at 220° C. isothermal). The peak indicated by reference numeral 120 is the peak for the compound having the structure:

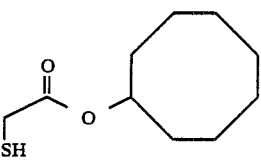

FIG. 13 is the NMR spectrum for the compound having the structure:

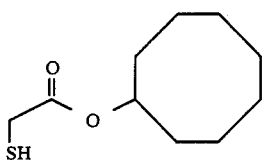

(Conditions: Field strength: 100 MHz; Solvent: CFCl₃).

EXAMPLE VI

PREPARATION OF CYCLOHEPTYL MERCAPTOACETATE

Reaction:

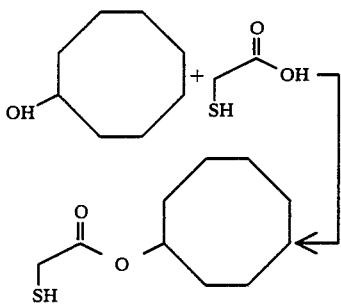

Into a 100 ml reaction flask equipped with stirrer, thermometer, reflux condenser and heating mantle are placed 28.5 grams of cycloheptanol; 9.2 grams of mercaptoacetic acid and 0.5 grams of paratoluene sulfonic acid. The reaction mass is heated to reflux and refluxed for a period of 10 hours. At the end of the 10 hour period, the reaction mass is washed with one 25 ml volume of water followed by drying over anhydrous sodium sulfate. The reaction mass is then distilled in a micro distillation apparatus yielding the compound having the structure

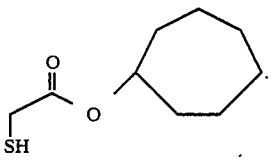

FIG. 14 is the GLC profile for the crude reaction product (Conditions: 8'×0.125" SE-30 column programmed at 100°–220° C. at 8° C. per minute). The peak indicated by reference numeral B 140 is the peak for the compound having the structure:

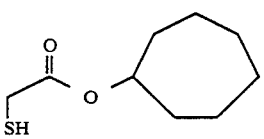

as confirmed by NMR, IR and mass spectral analyses.

The resulting product having the structure:

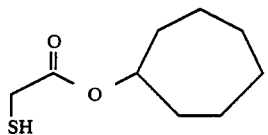

has a distinct roasted, sulfury and floral aroma and taste profile at 0.5 ppm.

FIG. 15 is the NMR spectrum for the compound having the structure:

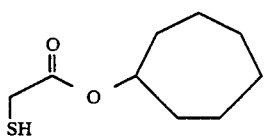

(Conditions: Field strength: 100 MHz; Solvent: CFCl₃).

EXAMPLE VII

PREPARATION OF (4'-t-BUTYLCYCLOHEXYL)-3-MERCAPTO-PROPIONATE

Reaction:

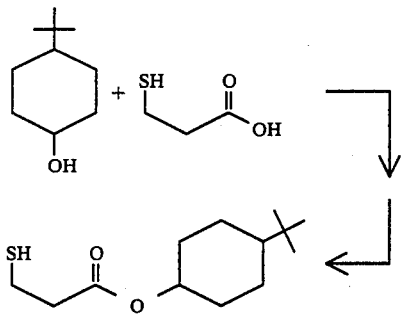

Into a 100 ml reaction flask equipped with reflux condenser, hot plate, spin bar and thermometer are placed 15.5 grams of 4-t-butylcyclohexanol; 0.5 grams paratoluene sulfonic acid and 15.5 grams of 3-mercaptopropionic acid.

The reaction mass is heated to reflux and maintained at reflux for a period of 12 hours. At the end of the 12 period, the reaction mass is distilled on a micro distillation apparatus yielding the compound having the structure:

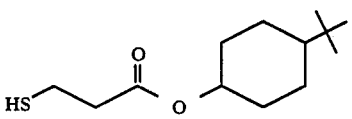

The resulting product having the structure:

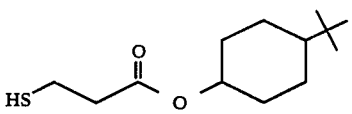

has a roasted and roasted meat aroma and taste profile at 0.001 ppm causing it to be useful in roasted meat, roasted nut and caramel flavored foodstuffs.

FIG. 16 is the NMR spectrum for the compound having the structure:

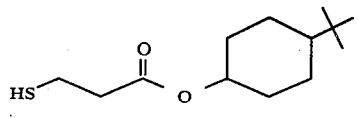

(Conditions: Field strength: 100 MHz; Solvent: CFCl₃).

EXAMPLE VIII

PREPARATION OF CYCLOPENTYL MERCAPTO ACETATE

Reaction:

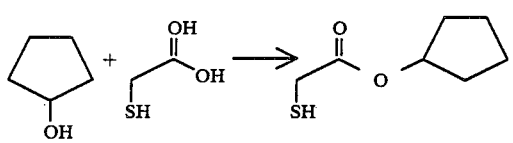

Into a 100 ml reaction flask equipped with stirrer, thermometer, reflux condenser and heating mantle are placed 21.5 grams of cyclopentanol and 9.2 grams of mercaptoacetic acid.

The reaction mass is heated to reflux and refluxed for a period of 9 hours. At the end of the 9 hour period, the reaction mass is fractionally distilled on a micro distillation apparatus to yield the compound having the structure:

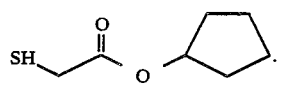

The compound having the structure:

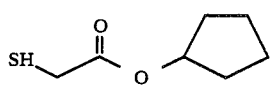

has a oniony and roasted onion aroma and taste profile at 0.2 ppm.

FIG. 17 is the GLC profile for the crude reaction product (Conditions: 8'×0.125" SE-30 column programmed at 100°-220° C. at 8° C. per minute). The peak indicated by reference numeral 170 is the peak for the compound having the structure:

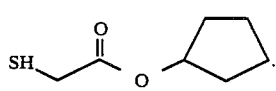

FIG. 18 is the NMR spectrum for the compound having the structure:

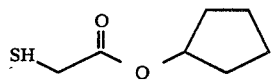

(Conditions: Field strength: 100 MHz; Solvent: CFCl₃).

EXAMPLE IX

PREPARATION OF CYCLOHEPTYL-2-MERCAPTOPROPIONATE

Reaction:

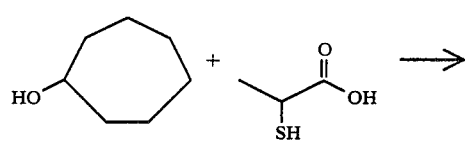

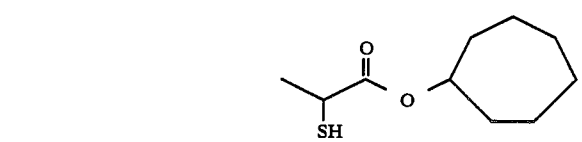

Into a 50 ml reaction flask equipped with stirrer, thermometer, reflux condenser and heating mantle are placed 11.4 grams cycloheptanol; 22 grams of 2-mercaptopropionic acid and 0.5 grams of paratoluene sulfonic acid. The reaction mass is heated to reflux and refluxed for a period of 10 hours. At the end of the 10 hour period, the reaction mass is distilled on a micro distillation apparatus to yield the compound having the structure:

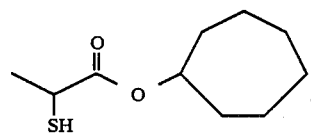

The compound having the structure:

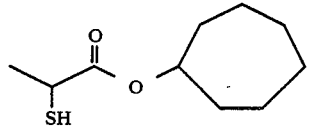

has a roasted, fruity, green, kiwi-like and citrus aroma and taste profile at 0.1 ppm causing it to be useful in kiwi, cashew and citrus flavored foodstuffs.

FIG. 19 is the GLC profile for the crude reaction product containing the compound having the structure:

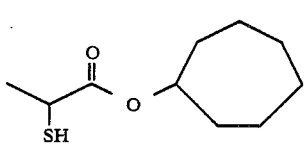

(Conditions: 8'×0.25" carbowax column programmed at 220° C. isothermal).

The peak indicated by reference numeral 190 is the peak for the compound having the structure:

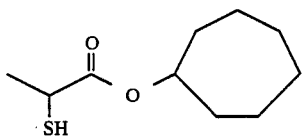

FIG. 20 is the NMR spectrum for the compound having the structure:

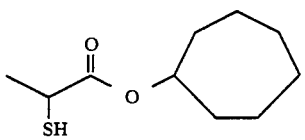

(Conditions: Field strength: 100 MHz; Solvent: CFCl$_3$).

EXAMPLE X

PREPARATION OF CYCLOPENTYL-2-MERCAPTOPROPIONATE

Reaction:

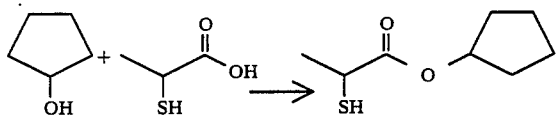

Into a 250 ml reaction flask equipped with stirrer, thermometer, reflux condenser and heating mantle are placed 86 grams of cyclopentanol; 25 grams of 2-mercaptopropionic acid; and 1 gram of paratoluene sulfonic acid. The reaction mass is heated to reflux and refluxed for a period of 8 hours. At the end of the 8 hour reflux period, the reaction mass is cooled and admixed with 200 ml diethylether followed by washing with two 100 ml volumes of 10% aqueous sodium carbonate and one 100 ml volume of water. The reaction mass is dried over anhydrous sodium sulfate and the solvent is recovered on a Buchi apparatus. The reaction mass is then micro distilled yielding the product having the structure:

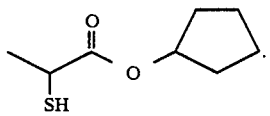

The product having the structure:

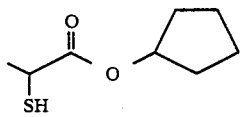

has a boiled corn, boiled green bean and cooked ham aroma and taste profile at 1 ppm.

FIG. 21 is the NMR spectrum for the compound having the structure:

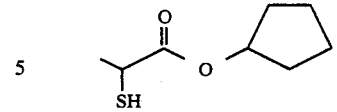

(Conditions: Field strength: 100 MHz; Solvent: CFCl$_3$).

EXAMPLE XI

PREPARATION OF CYCLOHEXYL-2-MERCAPTOPROPIONATE

Reaction:

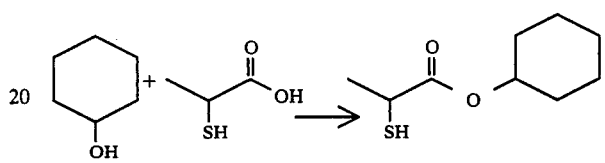

Into a 250 ml reaction flask equipped with stirrer, thermometer, reflux condenser and heating mantle are placed 100 grams of cyclohexanol; 26 grams of 2-mercaptopropionic acid and 0.5 grams of paratoluene sulfonic acid.

The reaction mass is heated to reflux and refluxed for a period of 9 hours. At the end of the 9 hour period, the reaction mass is cooled to room temperature and admixed with 200 ml diethylether followed by washing with two 100 ml volumes of 10% aqueous sodium carbonate and one 100 ml volume of water. The reaction mass is then dried over anhydrous sodium sulfate and the solvent is recovered on a Buchi evaporator. The reaction mass is then distilled on a micro distillation apparatus yielding the following fractions:

| Fraction No. | Vapor Temp. (°C.) | Liquid Temp. (°C.) | Vacuum mm/Hg. Pressure |
|---|---|---|---|
| 1 | 50/ | 55/ | 5 |
| 2 | 47 | 55 | 5 |
| 3 | 63 | 72 | 5 |
| 4 | 86 | 95 | 5 |
| 5 | 78 | 120 | 5 |

The resulting product having the structure:

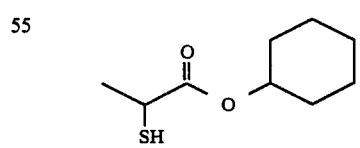

has a boiled corn, boiled green bean and cooked ham aroma and taste profile at 1 ppm causing it to be useful in augmenting or enhancing the aroma or taste of ham and boiled green vegetable flavored foodstuffs.

FIG. 22 is the GLC profile for the crude reaction product containing the compound having the structure:

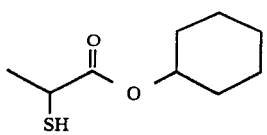

(Conditions: Carbowax column programmed at 100°–220° C. at 8° C. per minute). The peak indicated by reference numeral 220 is the peak for the compound having the structure:

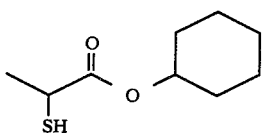

FIG. 23 is the NMR spectrum for the compound having the structure:

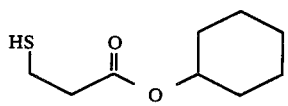

(Conditions: Field strength: 100 MHz; Solvent: CFCl₃).

EXAMPLE XII
PREPARATION OF CYCLOHEXYL-3-MERCAPTOPROPIONATE

Reaction:

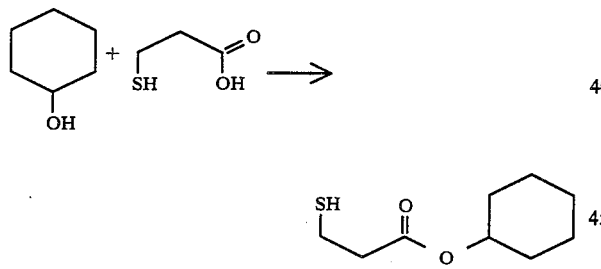

Into a 250 ml reaction flask equipped with stirrer, thermometer, reflux condenser and heating mantle are placed 100 grams of cyclohexanol; 26 grams of 3-mercaptopropionic acid and 0.5 grams of paratoluene sulfonic acid. The reaction mass is heated to reflux and refluxed for a period of 11 hours. At the end of the 11 hour period of refluxing, the reaction mass is cooled to room temperature. 200 ml Diethylether are added to the reaction mass. The reaction mass is then washed with two 100 ml volumes of 10% aqueous sodium bicarbonate solution followed by one 100 ml volume of water. The reaction mass is dried over anhydrous sodium sulfate and the solvent is recovered on a Buchi evaportor. The reaction mass is then micro distilled on a micro distillation apparatus yielding the following fractions:

| Fraction No. | Vapor Temp. (°C.) | Liquid Temp. (°C.) | Vacuum mm/Hg. Pressure |
|---|---|---|---|
| 1 | 50/ | 57/ | 5 |
| 2 | 54 | 62 | 5 |
| 3 | 90 | 70 | 5 |
| 4 | 97 | 108 | 5 |
| 5 | 90 | 120 | 5 |

The compound having the structure:

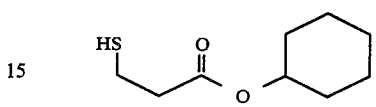

has a roasted, roasted sesame and roasted peanut aroma and taste profile at 0.1 ppm causing it to be useful in peanut, almond and sesame flavored foodstuffs.

FIG. 24 is the GLC profile for the crude reaction product.

FIG. 25 is the NMR spectrum for the compound having the structure:

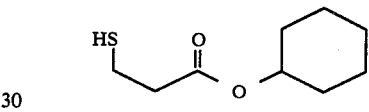

(Conditions: Field strength: 100 MHz; Solvent: CFCl₃).

EXAMPLE XIII
PREPARATION OF CYCLOHEPTYL-3-MERCAPTOPROPIONATE

Reaction:

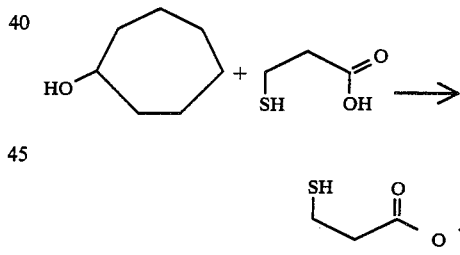

Into a 100 ml reaction flask equipped with stirrer, thermometer, reflux condenser and hot plate are placed 45.6 grams of cycloheptanol; 16 grams of 3-mercaptopropionic acid and 0.5 grams of paratoluene sulfonic acid. The reaction mass is heated to reflux and refluxed for a period of 12 hours. At the end of the 12 hour period, the reaction mass is cooled and distilled on a micro distillation apparatus yielding the compound having the structure:

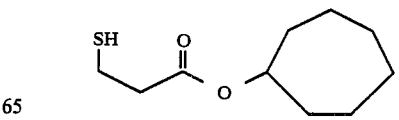

as confirmed by GLC, IR, NMR and mass spectral analyses.

The compound having the structure:

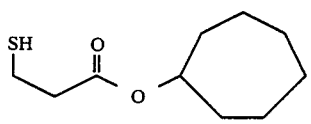

has a roasted, cashew juice, sulfury and roasted almond aroma and taste profile at 0.01 ppm causing it to be useful in cashew juice, roasted almond and caramel flavored foodstuffs.

FIG. 26 is the NMR spectrum for the compound having the structure:

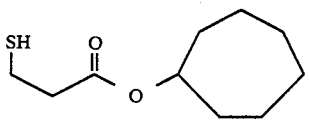

(Conditions: Field strength: 100 MHz; Solvent: CFCl₃).

EXAMPLE XIV

PREPARATION OF CYCLOHEXYL(4-METHYLTHIO)BUTYRATE

Reaction:

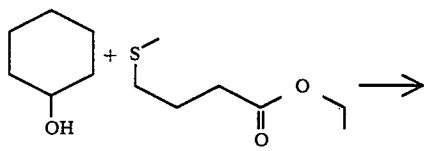

Into a 250 ml reaction flask equipped with magnetic stirrer, heating mantle, nitrogen sparger and reflux condenser are placed 10 grams cyclohexanol; 8.1 grams of methyl(4-methylthio)butyrate; and 0.5 grams of sodium methoxide (25% in methyl alcohol). The reaction mass is heated to 100° C. and maintained at 100° C. for a period of 15 minutes. At the end of the 15 minute period, the reaction mass is cooled and transferred to a separatory funnel where 45 ml of methylene chloride is added. The resulting mixture is washed with two 50 ml portions of water. The methylene dichloride layer is then separated and dried over anhydrous sodium sulfate and distilled on a micro distillation apparatus yielding the following fractions:

| Fraction No. | Vapor Temp. (°C.) | Liquid Temp. (°C.) | Vacuum mm/Hg. Pressure |
|---|---|---|---|
| 1 | 30/80 | 33/38 | 5 |
| 2 | 135 | 155 | 5 |
| 3 | 135 | 195 | 5 |
| 4 | 130 | 220 | 5 |

The compound having the structure:

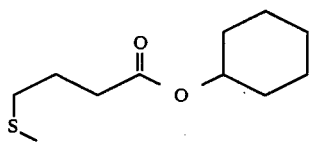

has a pineapple and green aroma and taste profile at 0.2 ppm causing it to be useful in pineapple flavored foodstuffs.

FIG. 27 is the GLC profile for Fraction 4 of the foregoing distillation (Conditions: 8'×0.25" carbowax column programmed at 220° C. isothermal).

FIG. 28 is the GLC profile for Fraction 3 of the foregoing distillation (Conditions: 8'×0.25" carbowax column programmed at 220° C. isothermal).

FIG. 29 is the NMR spectrum for the compound having the structure:

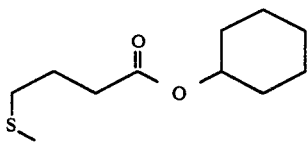

(Conditions: Field strength: 100 MHz; Solvent: CFCl₃).

EXAMPLE XV

PREPARATION OF CYCLOOCTYL-3-MERCAPTOPROPIONATE

Reaction:

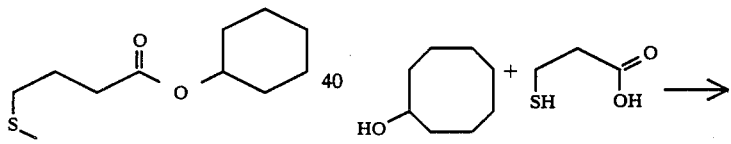

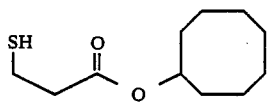

Into a 100 ml reaction flask equipped with reflux condenser, hot plate and spin bar are placed 45.6 grams of cyclooctenol; 16 grams of 3-mercaptopropionate and 0.5 grams of paratoluene sulfonic acid. Using a hot plate, the reaction mass is heated to reflux and reflux is continued for a period of 9 hours. At the end of the 9 hour period, the reaction mass is cooled to room temperature and micro distilled on a micro distillation apparatus yielding the compound having the structure:

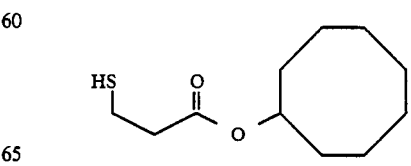

as confirmed by NMR, IR and mass spectral analyses. The resulting product having the structure:

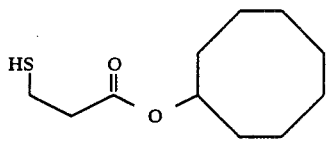

has a roasted, sulfury, concord grape and burnt potato skin aroma and taste profile at 0.1 ppm causing it to be useful in potato and concord grape flavored foodstuffs.

FIG. 30 is the NMR spectrum for the compound having the structure:

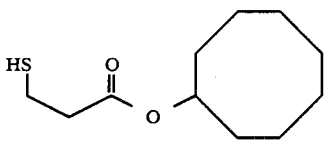

(Conditions: Field strength: 100 MHz; Solvent: CFCl$_3$).

EXAMPLE XVI

PREPARATION OF CONCORD GRAPE JAM

At the rate of 0.1 ppm the compound having the structure:

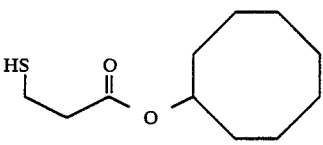

prepared according to Example XV and the compound having the structure:

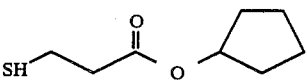

prepared according to Example IV(B) are added separately to SMUCKER'S ® grape jam (manufactured by the J. M. Smucker Company of Orrville, Ohio 44667). Each of the compounds prepared according to Example XV and IV(B) imparts a very natural concord grape nuance to the grape jam causing it to be preferred by a bench panel of five members. Each of the members of the bench panel is employed by International Flavors & Fragrances Inc., the assignee of the instant application. Each of the members of the bench panel did not know the nature of the materials being compared and the meaning of the results ascertained. The preference is a unanimous preference.

EXAMPLE XVII

The substance having the structure:

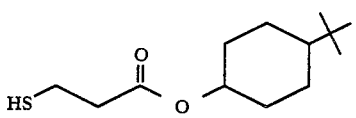

prepared according to Example VII is added to a 2% solution of Wyler's "Beef Flavored Instant Bouillon" (manufactured by Wyler Foods, a Division of Borden, Inc., Chicago, Ill.):

Ingredients salt;
hydrolyzed vegetable protein;
malto dextrin;
sugar;
beef fat;
water;
monosodium glutamate;
flavorings;
corn sugar;
beef extract;
caramel color;
hydrogenated vegetable fat; and
U.S. certified food color at the rate of 0.001 ppm.

The resulting flavor can be described as "beef with excellent roasted meat, roasted nut and caramel-like nuances". The roasted nuances have a very natural like flavor imparted by the compound having the structure:

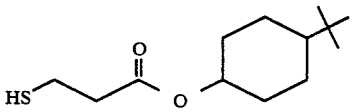

prepared according to Example VII.

EXAMPLE XVIII

To GOYA ® guava jelly (manufactured by Goya Foods Inc. of Secaucus, N.J. 07094) containing:
guava fruit;
guava juice;
sugar;
corn syrup;
pectin;
citrus acid;
is placed at levels of 0.1 ppm and 0.5 ppm the compound having the structure:

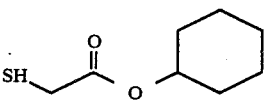

prepared according to Example II.

The resulting guava jelly has an excellent durian flavor with grapefruit nuances which render the jelly more aesthetically pleasing to a panel of five members. The panel of five members unanimously prefer the guava jelly containing the compound having the structure:

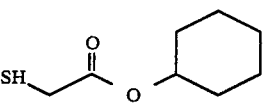

over the guava jelly without the compound having the structure:

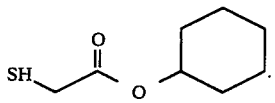

EXAMPLE XIX

The compound having the structure:

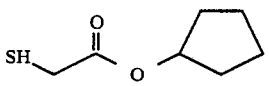

prepared according to Example VIII is dissolved in 95% ethanol to provide a 2% solution and is held at room temperature for 24 hours. It is then diluted with water and the water solution is added to a chicken broth to obtain a concentration of 2.5 ppm. It is found that the chicken taste is deepened and a light onion after taste is added. Increasing the concentration to 5 ppm adds an onion aroma and a roasted onion taste is dominating.

It is judged that the flavor additive having the structure:

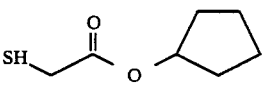

can replace flavors where roasted onion is used. It may also be used to supplement other onion flavors containing:
allyl propenyl disulfide;
allyl propenyl trisulfide;
diallyl disulfide;
allyl methyl disulfide; and
allyl methyl trisulfide.

EXAMPLE XX

Separately, the substances described as follows:

Substance "A"

The compound having the structure:

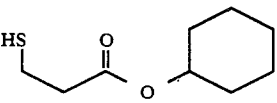

prepared according to Example XII.

Substance "B"

The compound having the structure:

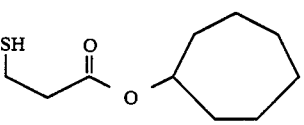

prepared according to Example XIII.

Substance "C"

The compound having the structure:

prepared according to Example IV(B).

Substance "D"

The compound having the structure:

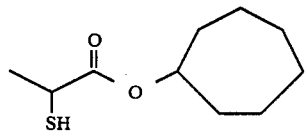

prepared according to Example IX.

Substance "E"

The compound having the structure:

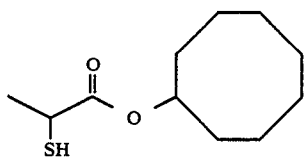

prepared according to Example III.

are added, respectively at the levels of 0.1 ppm, 0.01 ppm, 0.1 ppm, 0.1 ppm and 1 ppm to SMUCKER'S ® natural peanut butter produced by the J. M. Smucker Company of Orrville, Ohio 44667.

The compound having the structure:

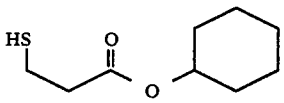

prepared according to Example XII imparts a long-lasting natural character to the peanut butter even after it is maintained in an open jar in a refrigerator for 3 weeks.

The compound having the structure:

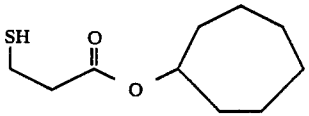

prepared according to Example XIII imparts a long-lasting cashew nuance to the peanut butter making it more aesthetically pleasing.

The compound having the structure:

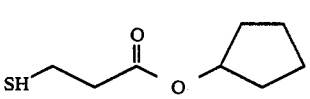

produced according to Example IV(B) imparts a cashew and almond nuance to the peanut butter in a long-lasting manner making it more aesthetically pleasing.

The compound having the structure:

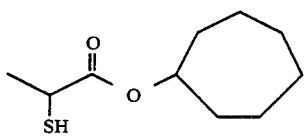

imparts a cashew nuance to the peanut butter making it more aesthetically pleasing.

The compound having the structure:

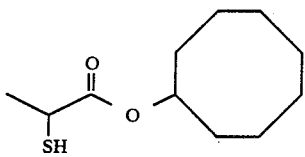

prepared according to Example III imparts a fresh long-lasting, natural roasted character to the peanut butter and causes it to be "natural tasting" for a period of 3 weeks even if the peanut butter is left in an open jar in a refrigerator.

A bench panel of five members unanimously prefers the peanut butters containing the cycloalkyl esters of mercaptoalkanoic acids set forth above over peanut butter not containing such materials. Each of the members of the bench panel is an employee of International Flavors & Fragrances Inc., the assignee of the above-identified application and each of the members of the bench panel did not know the nature of the materials being compared and the meaning of the results ascertained.

EXAMPLE XXI

Separately, the substances is described as follows:

Substance "F"

The compound having the structure:

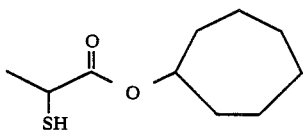

prepared according to Example IX.

Substance "G"

The compound having the structure:

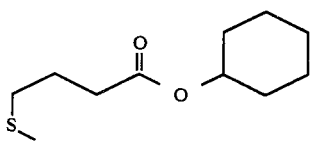

prepared according to Example XIV.

Substance "H"

The compound having the structure:

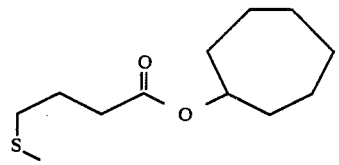

prepared according to Example I(A).

Substance "J"

The compound having the structure:

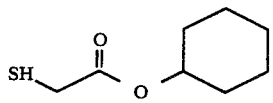

prepared according to Example II.

Substance "K"

The compound having the structure:

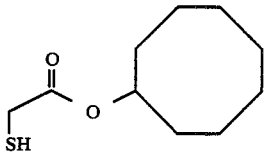

prepared according to Example V.

are added at the rates of 0.1 ppm, 0.2 ppm, 0.1 ppm, 1 ppm and 0.5 ppm, respectively, to (a) ACME ® unsweetened grapefruit juice made from concentrate (distributed by the American Stores Buying Company of Salt Lake City, Utah 84130); and (b) SMUCKER'S ® sweet orange marmalade (manufactured by the J. M. Smucker Company of Orrville, Ohio 44667).

The compound having the structure:

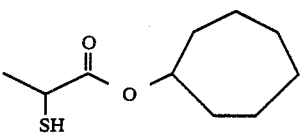

prepared according to Example IX imparts an intense, Kiwi aroma and taste nuance to the grapefruit juice and to the sweet orange marmalade making it more aesthetically pleasing to a blind bench panel of five members.

The compound having the structure:

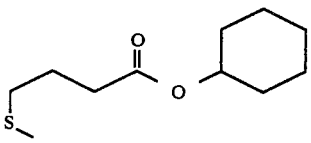

prepared according to Example XIV imparts an intense pineapple aroma and taste to the grapefruit juice and to the sweet orange marmalade thereby making it more aesthetically pleasing (unanimous opinion) to a blind bench panel of five members.

The compound having the structure:

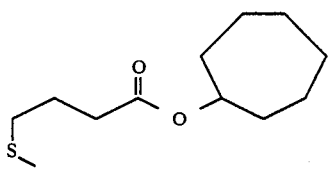

prepared according to Example I(A) imparts an intense pineapple aroma and taste nuance to the grapefruit juice and to the sweet orange marmalade causing it to be unanimously preferred by a blind bench panel of five members.

The compound having the structure:

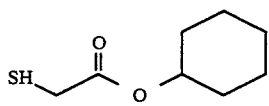

imparts a durian note to the grapefruit juice and to the sweet orange marmalade and also imparts an additional grapefruit nuance to the sweet orange marmalade making both the grapefruit juice and the sweet orange marmalade more aesthetically pleasing and causing them to be preferred by a blind bench panel of five members.

The compound having the structure:

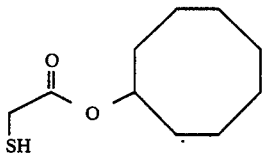

prepared according to Example V causes the grapefruit juice (even in an open tin container), refrigerated, to be more aesthetically pleasing than one not containing the compound having the structure:

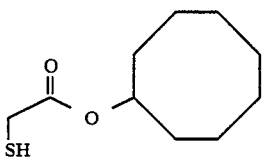

because the tin nuance from the tin container is "covered".

The compound having the structure:

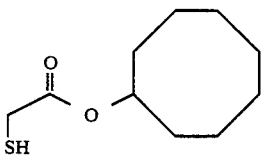

imparts a pleasant grapefruit nuance to the sweet orange marmalade causing it to be preferred by a blind bench panel of five members, unanimously.

EXAMPLE XXII

PREPARATION OF CYCLOPENTYL-4-(METHYLTHIO)BUTYRATE

Reaction:

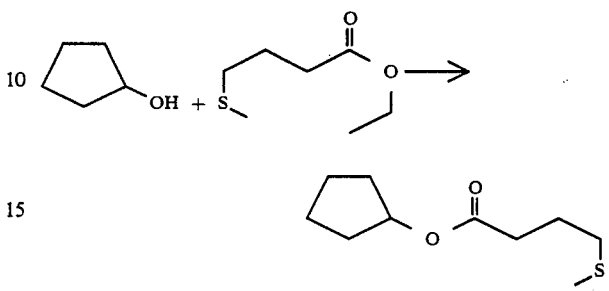

Into a 250 ml reaction flask equipped with stirrer, thermometer, reflux condenser and nitrogen sparging apparatus is placed 8.6 grams cyclopentanol; 8.1 grams of the ethyl ester of 4(methylthio)butyric acid and 0.5 grams of a 25% solution of sodium methoxide in methyl alcohol. The reaction mixture with stirring and with nitrogen sparging is heated to 100° C. and maintained at 100° C. for a period of 8 hours. At the end of the 8 hour period, the reaction mass is cooled and transferred to a separatory funnel. 50 ml Methylene dichloride is added. The reaction mass is washed with two 50 ml portions of water. The organic phase is dried over anhydrous sodium sulfate and distilled on a micro distillation apparatus yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 90/47 | 123/30 | 8-9/12 | 1.0 |
| 2 | 100 | 135 | 5 | 3.4 |
| 3 | 125 | 142 | 3 | 4.3 |
| 4 | 120 | 155 | 3 | 4.3 |
| 5 | 110 | 210 | 3 | 1.8 |

NMR, IR, GLC and mass spectral anaylses yield the information that the resulting product has the structure:

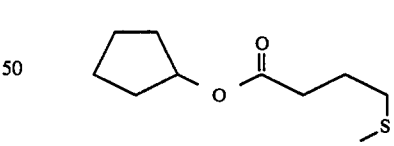

FIG. 31 is the GLC profile for the crude reaction product (Conditions: 8'×0.25" carbowax column programmed at 100°-120° C. at 8° C. per minute).

FIG. 32 is the GLC profile for Fraction 3 of the foregoing distillation.

FIG. 33 is the GLC profile for Fraction 4 of the foregoing distillation (Conditions: 8'×0.25" carbowax column programmed at 100°-220° C. at 8° C. per minute).

FIG. 34 is the GLC profile for Fraction 5 of the foregoing distillation (Conditions: Carbowax column programmed at 100°-220° C. at 8° C. per minute).

FIG. 35 is the NMR spectrum for the compound having the structure:

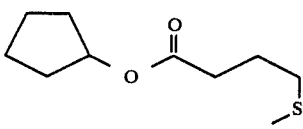

(Conditions: Field strength: 100 MHz; solvent: CFCl₃).

The resulting product having the structure:

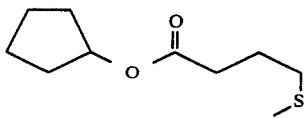

has an aesthetically pleasing pineapple and fruity aroma at 5 ppm.

EXAMPLE XXIII

PREPARATION OF CYCLOHEPTYL-4-(METHYLTHIO)BUTYRATE

Reaction:

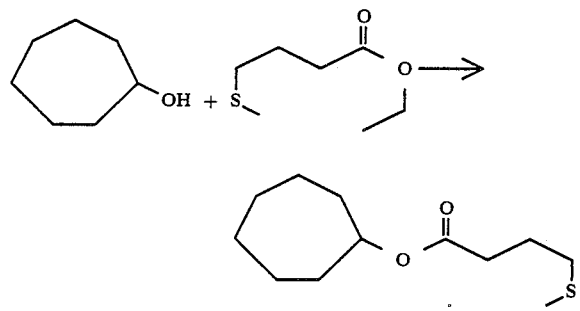

Into a 250 ml reaction flask equipped with magnetic stirrer, heating mantle, thermometer, nitrogen sparger and reflux condenser are placed 11.4 cycloheptanol; 8.1 grams of the ethyl ester of 4-(methylthio)butyric acid and 0.5 grams of a 25% methanolic solution of sodium methoxide.

The reaction mass is heated to 100° C. while sparging with nitrogen and maintained at that temperature for a period of 3 hours. At the end of the 3 hour period, the reaction mass is cooled to room temperature and transferred to a separatory funnel whereupon 50 ml methylene dichloride is added. The resulting mixture is washed with two 50 ml portions of water and the methylene chloride extract is dried over anhydrous sodium sulfate and distilled on a micro distillation column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 70/70 | 110/103 | 10 | 2.3 |
| 2 | 168 | 180 | 10 | 0.7 |
| 3 | 165 | 185 | 10 | 3.7 |
| 4 | 165 | 245 | 10 | 4.3 |

The resulting product is confirmed to have the structure:

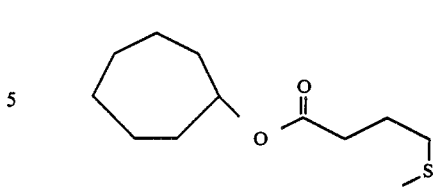

by NMR, IR, mass spectral and GLC anaylses.

FIG. 36 is the GLC profile for Fraction 4 of the foregoing distillation (Conditions: 8'×0.25" carbowax column programmed at 100°-220° C. at 8° C. per minute).

FIG. 37 is the NMR spectrum for Fraction 4 of the foregoing distillation containing the compound having the structure:

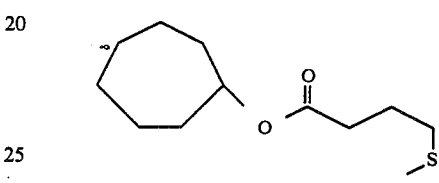

(Conditions: Field strength: 100 MHz; solvent: CFCl₃).

The resulting product having the structure:

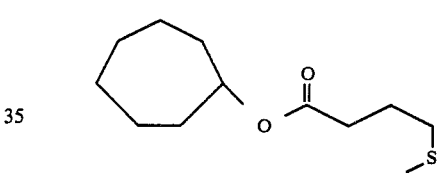

has an excellent fruity, pineapple and roasted aroma and taste profile at 0.2 ppm causing it to be useful in pineapple and peanut flavored foodstuffs.

EXAMPLE XXIV

At the rate of 5 ppm, the compound having the structure:

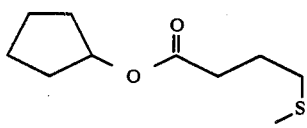

is added to SMUCKER'S ® orange marmalade. The compound having the structure:

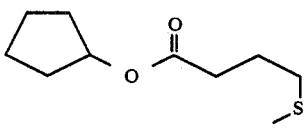

imparts a pleasant and aesthetically pleasing pineapple nuance to this orange marmalade causing it to be preferred unanimously by a bench panel of five members (blind panel not associated with the inventive entity of the instant application).

What is claimed is:

1. A process for augmenting or enhancing the aroma or taste of a foodstuff comprising the step of adding to said foodstuff from about 0.001 ppm up to about 250 ppm of at least one cycloalkyl ester of mercaptoalkanoic acid having the structure:

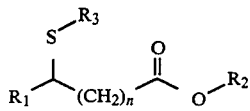

wherein $R_1$ represents hydrogen or methyl; $R_2$ represents mono $C_1$-$C_4$ alkyl substituted or unsubstituted $C_5$-$C_8$ cycloalkyl; $R_3$ represents hydrogen or methyl; and N represents 0, 1 or 2.

2. The process of claim 1 wherein the cycloalkyl ester of mercaptoalkanoic acid has the structure:

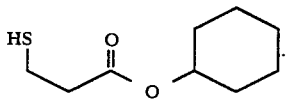

3. The process of claim 1 wherein the cycloalkyl ester of mercaptoalkanoic acid has the structure:

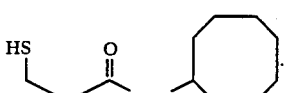

4. The process of claim 1 wherein the cycloalkyl ester of mercaptoalkanoic acid has the structure:

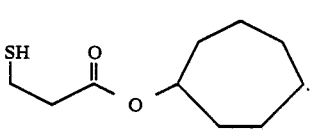

5. The process of claim 1 wherein the cycloalkyl ester of mercaptoalkanoic acid has the structure:

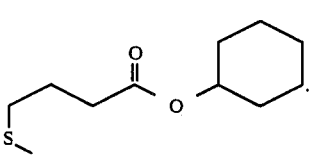

6. The process of claim 1 wherein the cycloalkyl ester of mercaptoalkanoic acid has the structure:

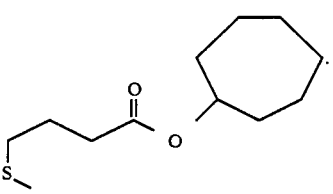

7. The process of claim 1 wherein the cycloalkyl ester of mercaptoalkanoic acid has the structure:

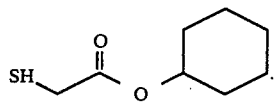

8. The process of claim 1 wherein the cycloalkyl ester of mercaptoalkanoic acid has the structure:

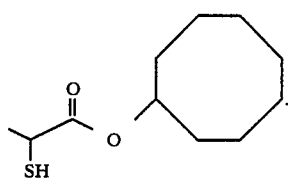

9. The process of claim 1 wherein the cycloalkyl ester of mercaptoalkanoic acid has the structure:

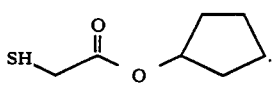

10. The process of claim 1 wherein the cycloalkyl ester of mercaptoalkanoic acid has the structure:

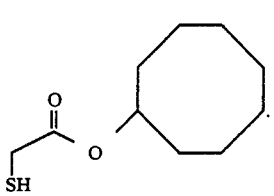

11. The process of claim 1 wherein the cycloalkyl ester of mercaptoalkanoic acid has the structure:

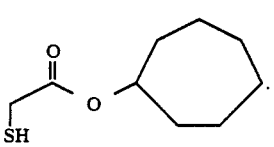

12. The process of claim 1 wherein the cycloalkyl ester of mercaptoalkanoic acid has the structure:

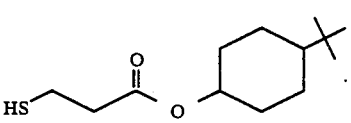

13. The process of claim 1 wherein the cycloalkyl ester of mercaptoalkanoic acid has the structure:

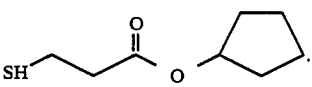

14. The process of claim 1 wherein the cycloalkyl ester of mercaptoalkanoic acid has the structure:

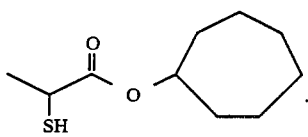
15. The process of claim 1 wherein the cycloalkyl ester of mercaptoalkanoic acid has the structure:
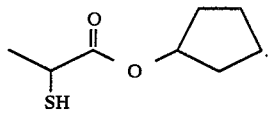
16. The process of claim 1 wherein the cycloalkyl ester of mercaptoalkanoic acid has the structure:
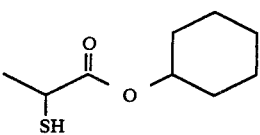
17. The process of claim 1 wherein the cycloalkyl ester of mercaptoalkanoic acid has the structure:
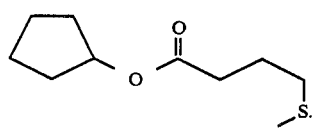
* * * * *

UNITED STATES PATENT AND TRADEMARK OFFICE
CERTIFICATE OF CORRECTION

PATENT NO. : 4,590,082
DATED : May 20, 1986
INVENTOR(S) : Alan O. Pittet, et al

It is certified that error appears in the above-identified patent and that said Letters Patent are hereby corrected as shown below:

Column 6, line 10 replace the structure thereat with the structure:

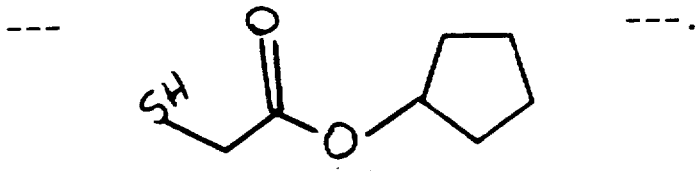

Column 6, line 35 replace the structure thereat with the structure:

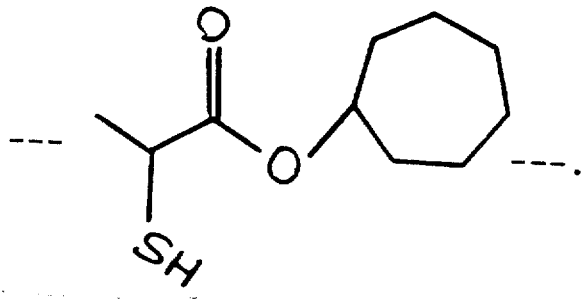

Column 6, lines 60-65, replace the structure thereat with the structure:

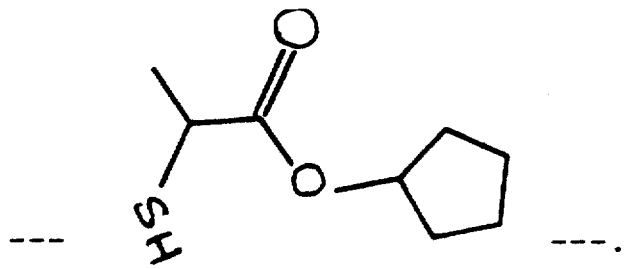

UNITED STATES PATENT AND TRADEMARK OFFICE
CERTIFICATE OF CORRECTION

PATENT NO. : 4,590,082

DATED : May 20, 1986

INVENTOR(S) : Alan O. Pittet

It is certified that error appears in the above-identified patent and that said Letters Patent is hereby corrected as shown below:

Column 7, line 5, replace the structure thereat with the structure:

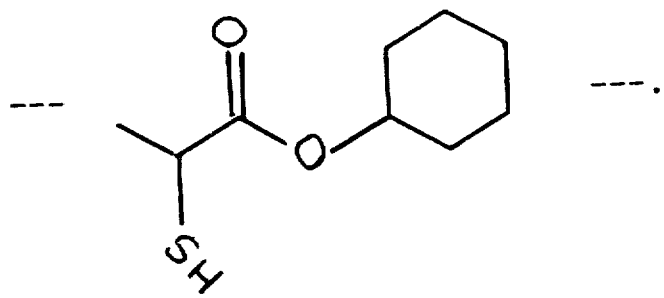

Column 7, line 30, replace the structure thereat with the structure:

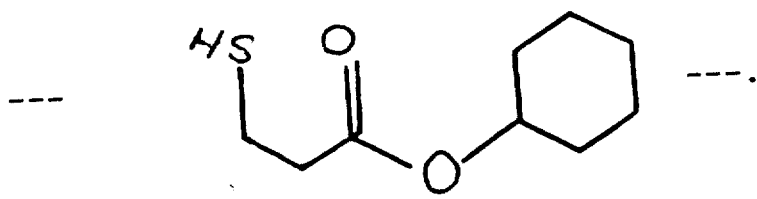

UNITED STATES PATENT AND TRADEMARK OFFICE
CERTIFICATE OF CORRECTION

PATENT NO. : 4,590,082
DATED : May 20, 1986
INVENTOR(S) : Alan O. Pittet, et al

It is certified that error appears in the above-identified patent and that said Letters Patent is hereby corrected as shown below:

Column 7, line 50, replace the structure thereat with the structure:

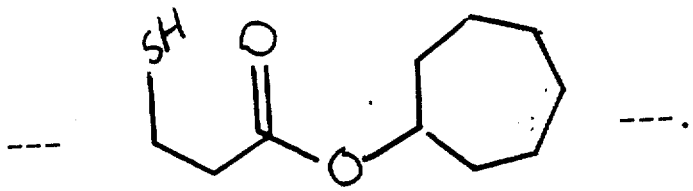

Signed and Sealed this

Sixteenth Day of September 1986

[SEAL]

Attest:

DONALD J. QUIGG

Attesting Officer

Commissioner of Patents and Trademarks